(12) United States Patent
Thie et al.

(10) Patent No.: US 9,518,131 B2
(45) Date of Patent: Dec. 13, 2016

(54) GENERATING METAL ION BINDING PROTEINS

(71) Applicant: Miltenyi Biotec GmbH, Bergisch Gladbach (DE)

(72) Inventors: Holger Thie, Cologne (DE); Kristina Reck, Kurten (DE); Volker Nolle, Kurten (DE)

(73) Assignee: Miltenyi Biotech GmbH, Bergisch Gladbach (DE)

( * ) Notice: Subject to any disclaimer, the term of this patent is extended or adjusted under 35 U.S.C. 154(b) by 0 days.

(21) Appl. No.: 14/242,725

(22) Filed: Apr. 1, 2014

(65) Prior Publication Data

US 2014/0296491 A1 Oct. 2, 2014

(30) Foreign Application Priority Data

Apr. 2, 2013 (EM) .................................... 13161984

(51) Int. Cl.
| | | |
|---|---|---|
| G01N 33/53 | (2006.01) | |
| C07K 16/44 | (2006.01) | |
| C07K 16/28 | (2006.01) | |

(52) U.S. Cl.
CPC ........... C07K 16/44 (2013.01); C07K 16/2815 (2013.01); C07K 2317/515 (2013.01); C07K 2317/56 (2013.01)

(58) Field of Classification Search
None
See application file for complete search history.

(56) References Cited

U.S. PATENT DOCUMENTS

| | | | |
|---|---|---|---|
| 5,011,912 A | 4/1991 | Hopp et al. | |
| 6,111,079 A | 8/2000 | Wylie et al. | |
| 2007/0065444 A1 | 3/2007 | North et al. | |
| 2011/0118443 A1* | 5/2011 | Sabbadini .............. | G01N 33/92 530/387.3 |
| 2011/0182817 A1 | 7/2011 | Matsuura et al. | |

FOREIGN PATENT DOCUMENTS

| | | |
|---|---|---|
| WO | WO-87/05912 A1 | 10/1987 |
| WO | WO-88/04692 A1 | 6/1988 |
| WO | WO-2006/068953 A2 | 6/2006 |
| WO | WO 2006/068953 A3 | 6/2006 |

OTHER PUBLICATIONS

Kwon et al. (Current Protocols in Protein Science 6.10.1-6.10.14, Feb. 2009, John Wiley & Sons, Inc.).*
Zhou et al. (PNAS, 2005, vol. 102, No. 41, pp. 14575-14580 and supplemental Fig. 7.*
IGKV17-121*01 V-Kappa (AJ231258), downloaded from www.imgt.org, pp. 1-2, last updated Dec. 21, 2012.*
Jackson et al. (J Immunol 1995; 154:3310-3319).*
Bajaj, S.P. et al. (Jan. 1992). "Antibody-Probed Conformational Transitions in the Protease Domain of Human Factor IX Upon Calcium Binding and Zymogen Activation: Putative High-Affinity $Ca^{2+}$-Binding Site in the Protease Domain," Proc. Natl. Acad. Sci. USA 89:152-156.
Einhauer, A. et al. (2001). "Affinity of the Monoclonal Antibody M1 Directed Against the FLAG Peptide," J. Chromatogr. A 921:25-30.
Erasmus, M.F. (2012). "Characterization of the Metal Binding by the Anti-Sphingosine-1-Phosphate Antibody LT1002," A Thesis Presented to the Faculty of San Diego State University, pp. 1-53.
Fanning, S.W. et al. (May 13, 2011). "A Combinatorial Approach to Engineering a Dual-Specific Metal Switch Antibody," Biochemistry 50:5093-5095.
Hopp, T.P. et al. (1996). "Metal-Binding Properties of a Calcium-Dependent Monoclonal Antibody," Mol. Immunol. 33(7/8):601-608.
Kong, T. et al. (2012). "Preparation of Specific Monoclonal Antibodies Against Chelated Copper Ions," Biol. Trace Elem. Res. 145,388-395.
Lefranc, M-P. (1999). "The IMGT Unique Numbering for Immunoglobulins, T-Cell Receptors, and Ig-Like Domains," The Immunologist 7(4):132-136 (1999).
Murtaugh, M.L. et al. (2011, e-pub. Jul. 15, 2011). "A Combinatorial Histidine Scanning Library Approach to Engineering Highly pH-Dependent Protein Switches," Protein Sci. 20:1619-1631.
Roberts, V.A. et al. (Jan. 1995). "Metalloantibody Design," FASEB J. 9:94-100. Wojciak, J.M. et al. (Oct. 20, 2009). "The Crystal Structure of Sphingosine-1-Phosphate in Complex With a Fab Fragment Reveals Metal Bridging of an Antibody and Its Antigen," Proc. Natl. Acad. Sci. USA 106(42):17717-17722.
Zhou, T. et al. (Oct. 11, 2005). "Interfacial Metal and Antibody Recognition," Proc. Natl. Acad. Sci. USA 102(41):14575-14580.
Adams, J.C. et al. (2011, e-pub. Aug. 29, 2011). "The Thrombospondins," CSH Perspectives 3:1-29.
Babu, C.S. et al. (Apr. 11, 2013). "Differential Role of the Protein Matrix on the Binding of a Catalytic Aspartate to $Mg^{2+}$ vs $CA^{2+}$: Application to Ribonuclease H," JACS 135:6541-6548.

* cited by examiner

Primary Examiner — Zachary Skelding
(74) Attorney, Agent, or Firm — Morrison & Foerster LLP

(57) ABSTRACT

The present invention provides for a method for generating a metal ion binding protein, the method comprising a) integrating the amino acid sequence DDD into CDR1 of a light chain variable region of an antibody or fragment thereof; and b) combining the sequence of step a) with a heavy chain variable region of an antibody or fragment thereof; and c) isolating the protein. Also provided is the use of metal ion binding proteins generated by the method of the present invention for isolation and purification of proteins and for the reversible labeling of a target molecule. Also provided is a metal ion binding anti-CD8 protein.

3 Claims, 16 Drawing Sheets

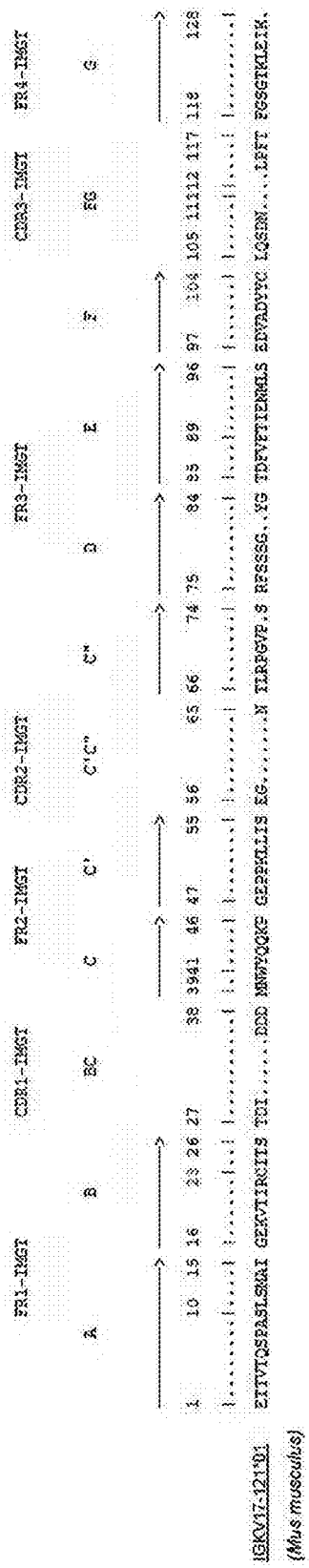

FIG1G

```
                    FR1-IMGT              CDR1-IMGT         FR2-IMGT        CDR2-IMGT            FR3-IMGT                                    CDR3-IMGT      FR4-IMGT

A         B          BC       C'              C'C"            C"    D               E               F                    FG                    G
             1    10   15  16    23 26 27  38 3941 46 47   55 56  65 66    74 75 84 85  89       96 97          104 105 21112 117 118                       128
LT1002       ETTVTQSPASLSMAI GEKVTIRCIITS TDI......DDD MRWFQQKP GEFPKLLIS EG......N ILRPGVP.S RFSSSG...YG IDFLFTIENMLS EDVADYYC LQSDN....LPFT FGSGTKLEIK
IGKV17S1*01  ETTVTQSPASLSMAV GEKVSISCKTS TDI......DDD MNWYQQRS GEAPKLLIS EG......N TLRPGVP.S RFSSSG...YG IDFVFTIENVLL GDEGYYC QQSDMVP       FT FGSGTKLEIK
(Rattus norvegicus)      V           T                     F P  P N         I         L            L    B M S E VAD     L          T  L
```

FIG1H

```
                            CDR1                               CDR2                                    CDR3
IGKV17-121*01  ETTVTQSPASLSMAIGEKVTIRCITS TDIDDD MNWYQQKPGEPPKLLIS EGN TLRPGVPSRFSSSGYGTDFVFTIENMLSEDVADYYC LQSDNLPFT FGSGTKLEIK
Q425 VL        ..............V............T.......................FF..............I........L.....................T..L............
LT1002 VL      .............................................F.....N..........L...................................................
```

FIG3

| Antibody gene library | Cycle I | Cycle II | Cycle III | |
|---|---|---|---|---|
| | Trypsin | Trypsin | EDTA | Trypsin |
| 1a VL fix + VH repertoire (spleen) | 1.1×10$^6$ | 7.6×10$^6$ | 3.4×10$^6$ | 3.3×10$^6$ |
| 2a VL fix + VH repertoire (lymph nodes) | 2.8×10$^7$ | 7.2×10$^6$ | 1.8×10$^6$ | 2.3×10$^6$ |
| 1b VL + VH repertoire (spleen) | 9.6×10$^6$ | 2.1×10$^7$ | - | - |
| 2b VL + VH repertoire (lymph nodes) | 1.2×10$^7$ | 3.2×10$^7$ | - | - |

FIG4

| Antibody gene library | Cycle I | Cycle II | Cycle III | |
|---|---|---|---|---|
| | Trypsin | Trypsin | EDTA | Trypsin |
| 1a VL fix + VH repertoire (spleen) | 9.6×10$^6$ | 1.7×10$^6$ | 2.8×10$^6$ | 5.6×10$^7$ |
| 2a VL fix + VH repertoire (lymph nodes) | 5.7×10$^7$ | 9.2×10$^6$ | 3.6×10$^7$ | 2.1×10$^8$ |
| 1b VL + VH repertoire (spleen) | 2.1×10$^7$ | 1.4×10$^8$ | - | - |
| 2b VL + VH repertoire (lymph nodes) | 3.0×10$^7$ | 8.1×10$^7$ | - | - |

FIG5

| Antibody gene library | | Cycle IIa | Cycle IIb | Cycle IIIb |
|---|---|---|---|---|
| | | EDTA | EDTA | EDTA |
| 1a | VL fix + VH repertoire (spleen) | $3.2 \times 10^5$ | $3.5 \times 10^3$ | $3.0 \times 10^4$ |
| 2a | VL fix + VH repertoire (lymph nodes) | $2.8 \times 10^4$ | $1.8 \times 10^4$ | $8.4 \times 10^4$ |
| 1b | VL + VH repertoire (spleen) | $3.8 \times 10^5$ | $3.6 \times 10^5$ | $1.6 \times 10^6$ |
| 2b | VL + VH repertoire (lymph nodes) | $1.2 \times 10^5$ | $2.4 \times 10^5$ | $2.9 \times 10^6$ |

FIG6

| Antibody gene library | | Cycle IIa |
|---|---|---|
| | | EDTA |
| 1a | VL fix + VH repertoire (spleen) | $3.2 \times 10^5$ |
| 2a | VL fix + VH repertoire (lymph nodes) | $2.8 \times 10^4$ |
| 1b | VL + VH repertoire (spleen) | $3.8 \times 10^5$ |
| 2b | VL + VH repertoire (lymph nodes) | $1.2 \times 10^5$ |

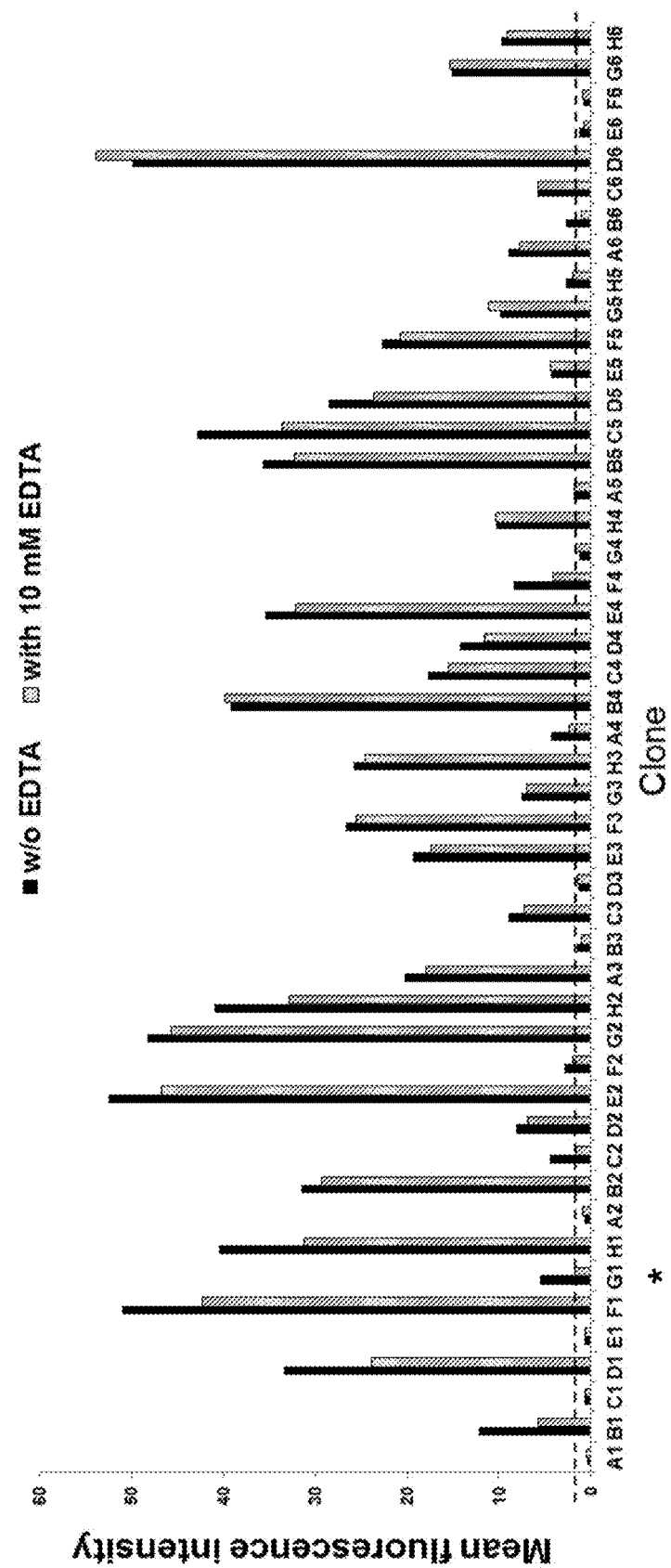

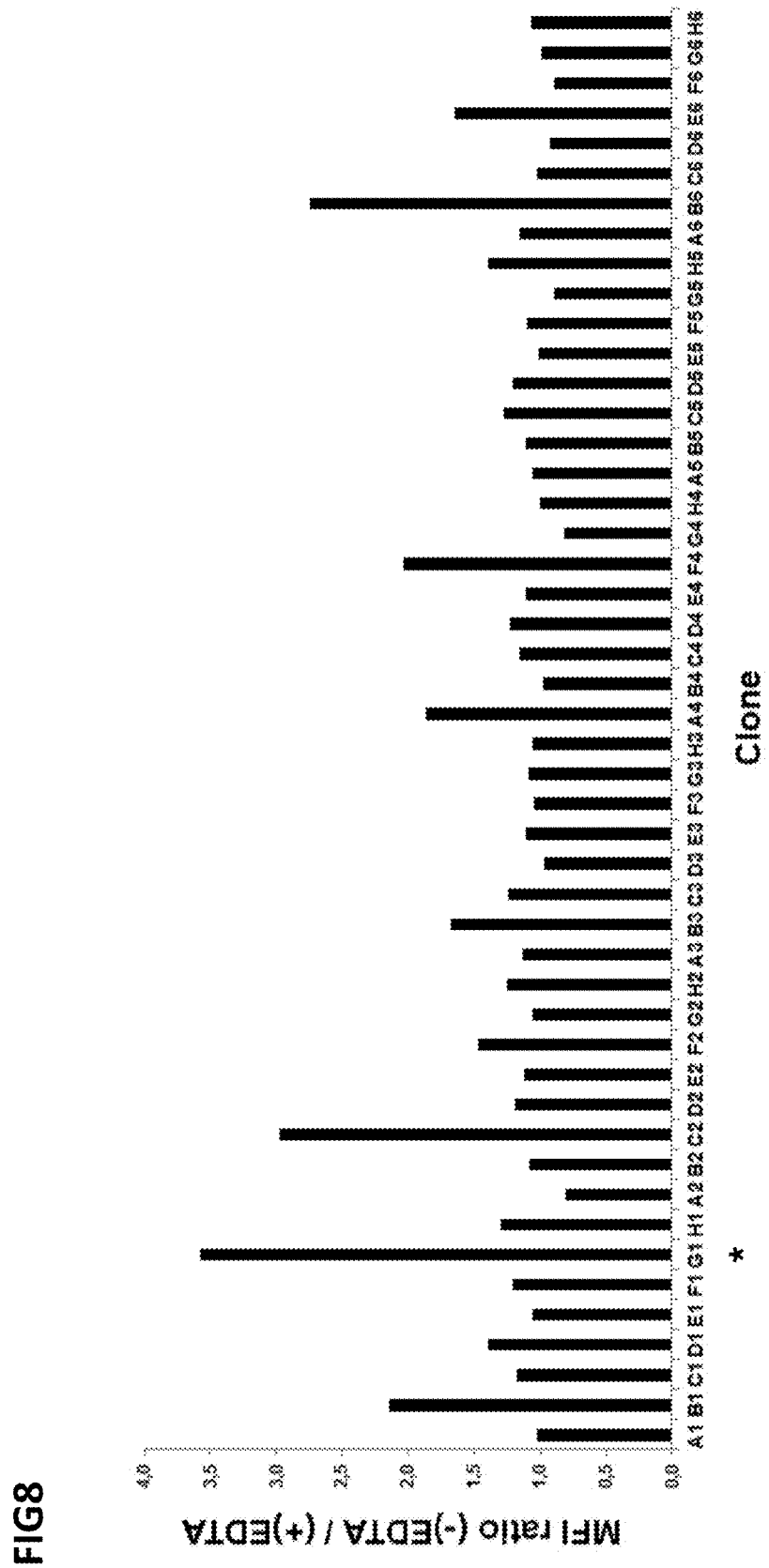

FIG14
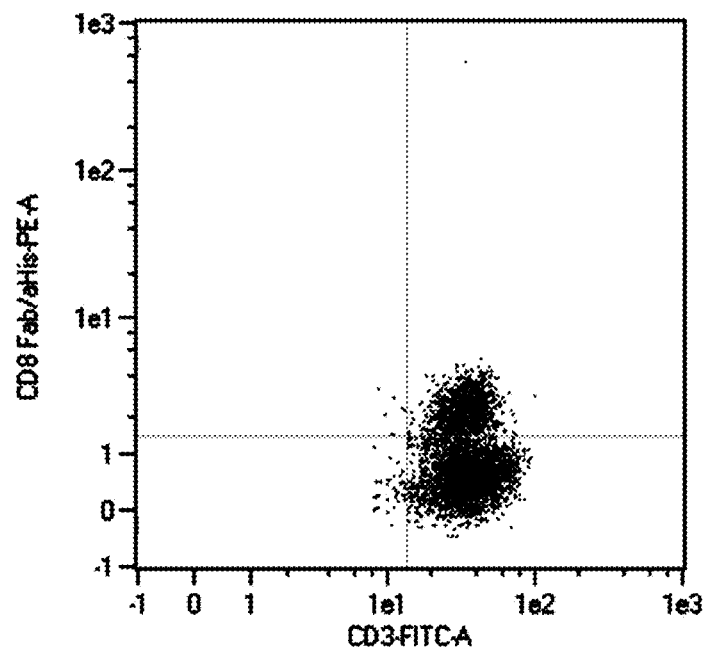
+ 10 mM EDTA
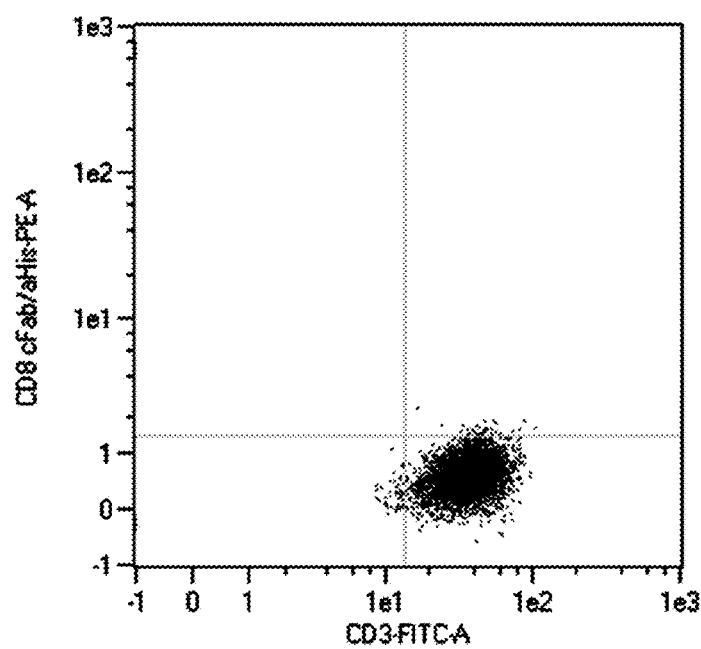

GENERATING METAL ION BINDING PROTEINS

CROSS REFERENCE TO RELATED APPLICATIONS

This application claims priority to European Application No. EP13161984.3, filed Apr. 2, 2013, incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 212302002500SubSeqList.txt, date recorded: Dec. 28, 2015, size: 11 KB).

FIELD OF THE INVENTION

The present invention relates generally to the field of generating proteins such as antibodies or fragments thereof, in particular to the process of generating metal ion binding proteins.

BACKGROUND OF THE INVENTION

Antibodies, also known as immunoglobulins (Ig), are essential components of the adaptive immune response of vertebrates. They are found in blood plasma or other bodily fluids, for example on mucosal areas performing recognition and neutralization of antigens. Antigens are mostly foreign substances such as viruses, bacteria or other pathogenic substances (toxins) invading the vertebrate body ("non-self" antigens), but sometimes these can also be autoantigens which are derived from molecules occurring in the body ("self" antigens).

The IgG antibody, the predominate antibody type in humans, is composed of four polypeptide chains: two identical heavy chains (HC) of about 50 kDa and two identical light chains (LC) with an approx. molecular weight of 25 kDa. While the isotype is specified by the kind of heavy chain, there also exist different light chains: λ (lambda) and κ (kappa).

Within the variable domains three regions show an especially high degree of variability: they are known as hypervariable or complementarity determining regions (VL CDR1-3 and VH CDR1-3) and alternate with four quite invariant framework regions (FR1-4). As a result of Ig domain folding the six CDR loops from VL and VH are in close spatial proximity and can interact with a certain region on the antigen (epitope) by different non-covalent interactions such as hydrogen bonds, van der Waals forces and ionic interactions.

Besides full-length antibodies, fragments of them have been developed. The most common antibody fragments are Fab (fragment antigen binding) and scFv (single chain fragment variable). The Fab fragment is composed of antibody light chain (VL and CL) connected by a disulfide bond to a part of the heavy chain (VH and CH1). In contrast, the scFv fragment consists of variable domains of heavy and light chain fused by a short peptide linker. Fab fragments can be produced by proteolytic cleavage of an immunoglobulin with the enzyme papain, which cleaves the molecule in the hinge region and produces consequently two Fab fragments and one Fc fragment (fragment crystallizable). Today Fab fragments, as well as many other antibody fragments, are mainly generated via recombinant DNA technologies. Besides Fab and scFv, there exist so far a wide range of different antibody fragments formats such as dsFv, single domain fragments or diabodies with two possible specificities.

For the development of novel antibody specificities genetic information of whole antibody repertoires can be amplified and used for the generation of gene libraries, which are subsequently selected to identify single antibodies with desired properties. The success of this approach basically depends on size (complexity) and quality of the generated libraries. In general libraries can be divided into three different types: immune libraries from immunized animals or infected humans, naïve libraries from non-immunized donors and synthetic/semi-synthetic libraries constructed with degenerated oligonucleotides. Besides source of antibody repertoire, these libraries differ in required library size. In contrast to naïve or synthetic approaches, immune libraries require rather low complexities, because previous immunizations supply antibody genes after in vivo affinity maturation and increase the chance to isolate an antibody with desired specificity. Nevertheless, naïve or synthetic libraries are favorable in the generation of antibodies against for example self-antigens or non-immunogenic haptens, because they overcome immunological tolerance mechanisms.

The generation of recombinant antibodies based on antibody gene libraries requires strong and efficient selection systems, for example phage display. This selection system deals with the presentation of molecules on the surface of filamentous bacteriophages such as M13. Filamentous phages are viruses infecting Gram-negative bacteria such as, for example, *E. coli* via F-pili; the infection does not lead to cell lysis but to continuous release of assembled phage particles from infected cells.

The human CD8 molecule is a glycoprotein and cell surface marker expressed on cytotoxic T-cells (CTLs). These are a subset of T-lymphocytes and play an important role in the adaptive immune system of vertebrates. They are responsible for the elimination of virus-infected cells or other abnormal cells such as some tumor cells. These cells are specifically recognized via the T-cell receptor (TCR), which interacts with the certain antigen presented via MHC (major histocompatibility complex) class I on target cells.

In many protein interactions metal ions play an important role. About 20% of all antibody crystal structures contain metal ions, although most of these may be crystallization artifacts (Zhou et al., *Proc Natl Acad Sci USA* 102, 14575-14580 (2005)). There are publications describing antibodies with metal specificities, for example against chelated copper ions (Kong et al., *Biol Trace Elem Res* 145, 388-395 (2012)) or catalytic active metallo-antibodies (Roberts and Getzoff, *FASEB J* 9, 94-100 (1995)). Metal ions can also influence a certain conformational state in an antigen, which is selectively recognized by an antibody, for example a Ca2+ sensitive epitope in human factor IX (Bajaj et al., *Proc Natl Acad Sci USA* 89, 152-156 (1992)). Furthermore, the monoclonal M1 antibody directed against the FLAG peptide has been claimed to bind its antigen in a calcium dependent manner, allowing a release in immunoaffinity purifications with chelating agents such as EDTA (Hopp et al., *Mol Immunol* 33, 601-608 (1996)). However, M1 does not show any affinity differences of antibody-antigen interaction in the presence or absence of Ca2+, so this observation results in the assumption that the added EDTA forms a short transition state with less affinity and there is no real calcium dependency (Einhauer and Jungbauer, *J Chromatogr A* 921, 25-30 (2001)). In contrast to these findings, two publications determined the crystal structure of two calcium dependent antibodies which show calcium ions at the interface of antigen and antibody interaction (Zhou et al., *Proc Natl Acad Sci USA* 102, 14575-14580 (2005); and Wojciak et al., *Proc Natl Acad Sci USA* 106, 17717-17722 (2009)). First, Zhou et al. disclosed the calcium dependent human CD4 reactive monoclonal antibody Q425. The binding of this antibody was affected by $Ca^{2+}$ ions and to a lesser extent by $Sr^{2+}$ and $Cd^{2+}$ ions, but not or nearly negligible by $Mg^{2+}$, $Ba^{2+}$, $Mn^{2+}$, $Cu^{2+}$, $Co^{2+}$, $Ni^{2+}$, $Zn^{2+}$ and $K^+$ ions. In surface plasmon resonance experiments, a 55,000-fold affinity enhancement in the presence of 25 mM $Ca^{2+}$ compared to calcium-free conditions was determined. The protein structure revealed that a single calcium ion is primarily coordinated by negatively charged side chains of the amino acids aspartate and glutamate in the CDRs of the light chain. Besides these observations, Wojciak et al. disclosed the crystal structure of the α-sphingosine-1-phosphate (S1P) LT1009 protein in complex with its antigen, a lipid (non-protein), wherein LT1009 is a papain-generated Fab fragment of a humanized antibody. The structure showed an association of calcium ions with mainly glutamate side chains of CDRs of the light chain. A 100-fold change in affinity when calcium was present or absent was also reported. In both cases (Q425 and LT1009) calcium ions are bridging the interaction between antigen and antibody at their interface. Due to the $Ca^{2+}$ dependency the binding reaction of these antibodies to their binding partners such as a protein or a lipid is reversible under mild conditions, for example by the addition of EDTA. This property was generated accidentally and not intentionally; in both cases standard methods for generating antibodies were used without the intention to generate calcium ion dependent antibodies or antibody fragments.

In Erasmus (Thesis, San Diego State University (2012)) LT1002 is disclosed which is the murine pre-engineered antibody version of LT1009. LT1002 was analyzed and showed a tendency to bind $Ca^{2+}$ ions and to a smaller extent also $Mg^{2+}$ and $Ba^{2+}$ ions. This is not surprising since LT1002 is the pre-version of LT1009. The amino acid sequence of LT1002 is disclosed in U.S. Pat. No. 8,067,549.

Fanning et al. (*Biochemistry* 50, 5093-5095 (2011)) developed a synthetic library approach to generate a novel dual-specific antibody. Using a combinatorial histidine-scanning phage display library, potential metal binding sites were introduced throughout an anti-RNase A antibody interface. Stepwise selection of RNase A and metal binding produced a dual-specific antibody that retained near wild-type affinity for its target antigen while acquiring a competitive metal binding site for nickel that is capable of controlling the antibody-antigen interaction. The publication does not disclose if this approach using introduced histidine residues in the antibody/antigen interface also works with metal ions other than $Ni^{2+}$, because the authors showed that the metal site is specific for nickel as titrations performed in the presence of calcium ions did not show any appreciable change in the observed binding constant. Another major limitation of this approach is the fact that the resulting antibody shows the highest affinity to its antigen in the absence of metal ions, while addition on $Ni^{2+}$ partially decreases the affinity, excluding this approach for the generation of antibodies which bind their antigen in the presence of a metal ion and do not bind or release their antigen in the absence of the metal ion.

Using a similar approach, Murtaugh et al. (*Protein Sci* 20, 1619-1631 (2011)) used a combinatorial histidine library to introduce histidine residues into the binding interface of an anti-RNase A single domain VHH antibody. They generated a "switchable" antibody variant that binds to its antigen in a pH-dependent manner. Although such antibody variants can be useful for the controlled binding to its antigen in one situation (such as pH>7) and the controlled dissociation from the antigen in another situation (such as pH<5), the publication does not disclose how "switachble" antibodies can be generated which can be controlled with metal ions. There is also the disadvantage that these pH-dependent antibodies are not compatible with the strict requirements of cell culture conditions where cells are usually kept within a narrow pH range at nearly neutral pH.

U.S. Pat. No. 6,111,079 discloses a metal binding protein which selectively binds a complex of a heavy metal, such as lead cation, and glutathione. Mice were immunized with a glutathione/$Pb^{2+}$ complex, and monoclonal antibodies were generated by hybridoma technology. These antibodies were screened against their ability to bind a glutathione/$Pb^{2+}$ complex. The disclosure is directed to methods for detecting, removing, adding, or neutralizing heavy metals in biological and inanimate. These proteins have a high discrimination for lead cations and against other metallic cations. U.S. Pat. No. 6,111,079 does not teach which amino acids are de facto involved in lead cation binding. The method described in U.S. Pat. No. 6,111,079 has the disadvantage of generating only antibodies against a glutathione/$Pb^{2+}$ complex. Such a heavy metal binding antibody also has the disadvantage that it is not compatible with the strict requirements of cell culture conditions due to toxicity of the heavy metal $Pb^{2+}$.

The frequency of metal ion binding proteins which bind their binding partner such as an antigen in the presence of the metal ion and which can be released from the binding partner by removal or complexation of the metal ion by for example EDTA or EGTA seems to be rather low. For antibodies, Zhou et al. (2005) speculated that although ~20% of antibody crystal structures contain metal ions most of these are crystallization artifacts, and in other cases partially coordinated metal ions offer no or little advantage in terms of binding. Instead, for an antibody, a direct antigen binding usually seems to be preferred over interfacial metal coordination.

There is a need in the art for the targeted generation of metal ion binding proteins such as antibodies or fragments thereof in which metal ions such as $Ca^{2+}$ are bridging the interaction between the protein, e.g. an antibody, and the binding partner of the protein, e.g. an antigen, at their interface. This results in a binding between the metal ion binding protein and the binding partner of the protein which is reversible, depending on the presence or absence of the metal ion or a chelating or complexing reagent such as EDTA or oxalate, respectively.

All references cited herein, including patent applications and publications, are incorporated by reference in their entirety.

SUMMARY OF THE INVENTION

Antibodies or fragments thereof can be generated using methods known in the art such as antibody phage display. Surprisingly, it was now found that the hit rate of generating metal ion binding proteins, e.g. antibodies or fragments thereof, using such methods can be highly increased by involving a light chain variable region of an antibody having the amino acid sequence motif DDD (one-letter code, which is equal to Asp-Asp-Asp in three-letter code) within CDR1 and a further D (Asp) residue within CDR3 of the light chain (CDR-L1 and CDR-L3).

The murine germ line allele of the light chain of antibody IGKV17-121*01 (IMGT numbering scheme, Lefranc, *The Immunologist* 7, 132-136 (1999)) is fixed as a base sequence. In a next step the complete set of alleles of an immune library composed of variable region of heavy chains is added to the light chain in a combinatory approach, generating antibodies or fragments thereof which have a high diversity of combinations of IGKV17-121*01 and any heavy chain ("chain shuffling"). The diversity of the pool is generated by the heavy chains only. The pool may pass through a maturation in the sense of amino acid mutations in vivo or in vitro. Such antibodies or fragments thereof having a metal ion dependency on binding their antigen are enriched and isolated using proper technologies and screening methods. The metal ion binding protein derived by this method is therefore not restricted to a binding partner which itself binds metal ions per se.

BRIEF DESCRIPTION OF THE DRAWINGS

FIG. 1A shows IMGT Numbering scheme applied to murine IGKV17-121*01 allele (SEQ ID NO:1). FIG. 1B shows alignment of VL of Ca2+ dependent CD4 Q425 (SEQ ID NO:7) and closest murine (*mus musculus*) germ line gene IGKV17-121*01 (SEQ ID NO:1) with IMGT-numbering applied. FIG. 1G shows alignment of VL of Ca2+ binding anti-Sphingosine LT1002 (SEQ ID NO:8) and closest rat (*rattus norvegicus*) germ line gene IGKV17S1*01 (SEQ ID NO:3) with IMGT-numbering applied. FIG. 1H shows alignment of VL of Ca2+ binding anti-Sphingosine LT1002 (SEQ ID NO:8), VL of Ca2+ dependent CD4 Q425 (SEQ ID NO:7) and closest murine (*mus musculus*) germ line gene IGKV17-121*01 (SEQ ID NO:1) with IMGT-numbering applied.

FIG. 2A shows PCR products of VH repertoire after immunization with hCD8a protein FIG. 2A1: first PCR round with forward primer IGHV1-16, FIG. 2A2: second PCR round with forward primer IGHV1-16.SfiI). FIG. 2B shows PCR products of VH repertoire after immunization with human CD8+ cells FIG. 2B1: first PCR round with forward primer IGHV1-16, FIG. 2B2: second PCR round with forward primer IGHV1-16.SfiI).

FIG. 3 shows antibody phage titer (cfu) after different panning cycles (coated hCD8a). Cfu were determined in eluates of different panning cycles. Panning was started with $1 \times 10^{11}$ antibody phages.

FIG. 4 shows antibody phage titer (cfu) after different panning cycles (biotinylated hCD8a). Cfu were determined in eluates of different panning cycles. Panning was started with $1 \times 10^{11}$ antibody phages.

FIG. 5 shows antibody phage titer (cfu) after different panning cycles with previous depletion(s) of Ca2+ independent hCD8a binders (coated hCD8a). Cfu were determined in eluates of different panning cycles. Panning was started with $1 \times 10^{11}$ antibody phages.

FIG. 6 shows antibody phage titer (cfu) after different panning cycles with previous depletion(s) of Ca2+ independent hCD8a binders (biotinylated hCD8a). Cfu were determined in eluates of different panning cycles. Panning was started with $1 \times 10^{11}$ antibody phages.

FIGS. 7, 8, and 9 show flow cytometry results of screened clones after panning cycle 2b. Flow cytometry results of screened clones of library 2a from EDTA eluates after panning cycle IIb with triple depletion of Ca2+ independent hCD8a binders. After exclusion of dead cells and cell debris CD8+ cells were identified as a CD3+/CD4– cell population. hCD8-specific Fabs were detected by anti-polyhistidine-PE (anti-HIS-PE). Mean fluorescence intensities (MFI) of anti-HIS-PE staining were plotted to evaluate the influence of 10 mM EDTA. 75_A1 (uninoculated medium) and 75_C1 (anti-MUC1 scFv expressing clone) were negative controls, while 75_B1 (CD8 BW135/80) served as positive control. FIG. 7: MFI before and after addition of EDTA. FIG. 8: MFI ratio (−)EDTA/(+)EDTA. FIG. 9: Dot plots of clone KRR75_G1 before and after the addition of 10 mM EDTA.

FIG. 10: MFI before and after addition of EDTA. FIG. 11: MFI ratio (−)EDTA/(+)EDTA. FIG. 12: Dot plot of clone KRR77_D1 before and after the addition of 10 mM EDTA.

FIG. 14 shows flow cytometry results of PMBC staining with purified chimeric recombinant CD8 KRR75_G1. Fab was detected by anti-His-PE. Mean fluorescence intensities (MFI) of anti-His-PE staining were plotted to evaluate the influence of 10 mM EDTA on staining with certain chimeric Fab CD8 KRR75_G1.

DETAILED DESCRIPTION OF THE INVENTION

Figures 1C, 1D:
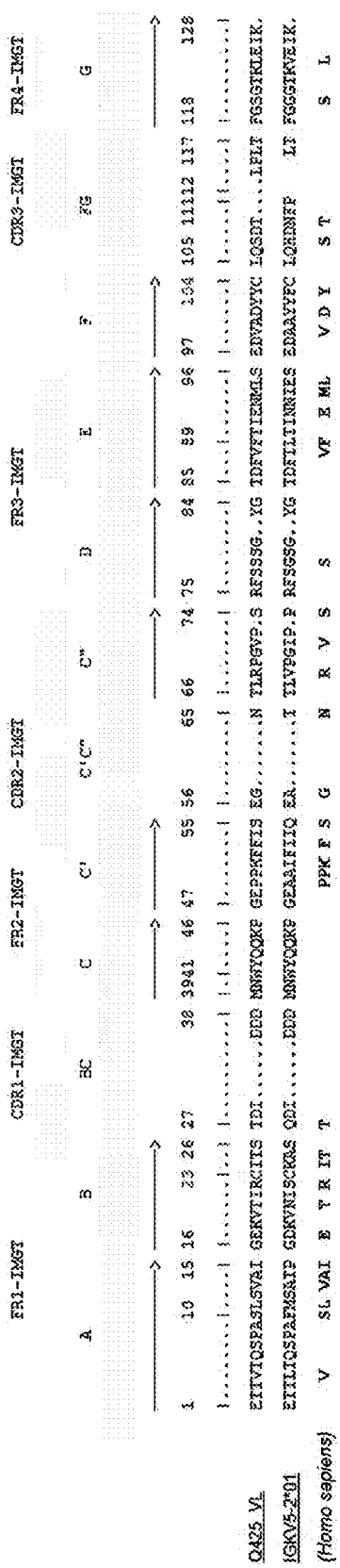
FIG. 1C shows alignment of VL of Ca2+ dependent CD4 Q425 (SEQ ID NO:7) and closest human (*homo sapiens*) germ line gene IGKV5-2*01 (SEQ ID NO:2) with IMGT-numbering applied.
FIG. 1D shows alignment of VL of Ca2+ dependent CD4 Q425 (SEQ ID NO:7) and closest rat (*rattus norvegicus*) germ line gene IGKV17S1*01 (SEQ ID NO:9) with IMGTnumbering applied.
Figure 1E:
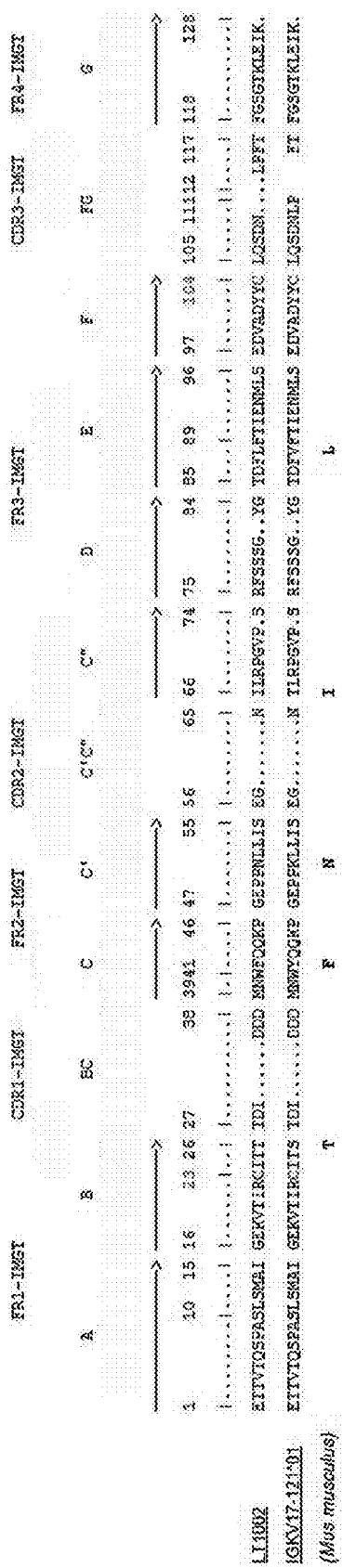
FIG. 1E shows alignment of VL of Ca2+ binding anti-Sphingosine LT1002 (SEQ ID NO:8) and closest murine (*mus musculus*) germ line gene IGKV17-121*01 (SEQ ID NO:1) with IMGT-numbering applied.
Figure 1F:
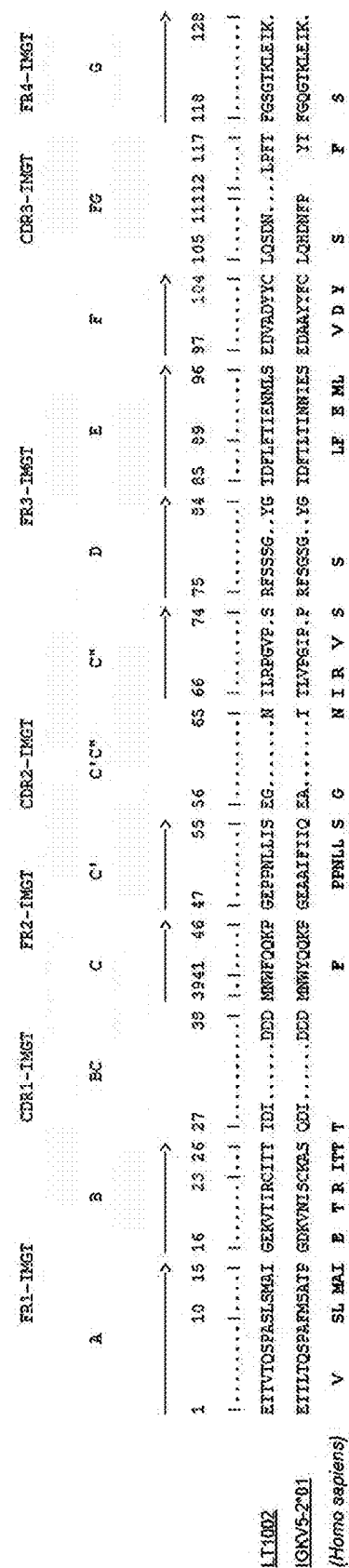
FIG. 1F shows alignment of VL of Ca2+ binding anti-Sphingosine LT1002 (SEQ ID NO:8) and closest human (*homo sapiens*) germ line gene IGKV5-2*01 (SEQ ID NO:10) with IMGT-numbering applied.

Surprisingly, a method was found which enables the targeted generation of metal binding proteins such as antibodies or fragments thereof.

Ca2+ dependency of binding was transferred to proteins such as antibodies or fragments thereof by using variable light chain germline sequence mIGKV17-121*01 (or a sequence derived therefrom) in combination with murine VH immune repertoires against an antigen such as human CD8 to generate antigen specific Ca2+ binding antibodies or fragments thereof.

Herein, the method is exemplified by the generation of hCD8 specific Ca2+ binding antibody fragments. Regularly, in anti-CD8 antibodies or fragments thereof Ca2+ ions do not interact with the paratope region of the antibody itself and therefore do not influence the affinity of antigen-antibody interaction.

After successful immunization of mice with recombinant hCD8a protein or hCD8+ cells, phagemid-based VH immune libraries were cloned in a chimeric Fab format harboring the fixed (Ca2+ binding) VL germline gene. A second antibody gene library containing fully shuffled VL- and VH-gene immune repertoires was simultaneously generated. Phage display selections with several panning cycles against hCD8a protein and the subsequent screening provided many hCD8 specific Fabs with high sequence similarity.

In addition, several selection strategies were performed to direct selections towards Ca2+ dependent hCD8a interactions. Beside presence of Ca2+ ions during phage display followed by an elution of binders using chelating agents such as EDTA, depletions of Ca2+ independent binders before the actual panning cycle were performed. As a result the clone KRR75_G1, characterized by an EDTA sensitive binding, was identified after a threefold depletion of Ca2+ independent binders prior to panning with final EDTA elution. Further panning and enrichment resulted in the isolation of further potential Ca2+ dependent candidate KRR77_D1. All EDTA sensitive clones were derived from libraries with fixed VL gene, meaning that mIGKV17-121*01 is linked with Ca2+ dependency and that it is possible to transfer this property to other antibody specificities. In addition, sequence analysis revealed that VH genes of potential Ca2+ binding Fabs completely differed from other isolated hCD8-specific Fabs.

Further flow cytometric analysis of clones KRR75_G1 and KRR77_D1 showed that in absence of EDTA a staining of human CD8+ cells was possible which resulted in a well-defined positive cell population. After addition of EDTA to this sample the staining was diminished instantly (within 60 seconds or less).

Therefore, it is an object of the present invention to provide a method for generating a metal ion binding protein, e.g. a calcium ion binding protein, the method comprising a) integrating the amino acid sequence DDD into CDR1 of a light chain variable region of an antibody or fragment thereof; and b) combining the sequence of step a) with a heavy chain variable region of an antibody or fragment thereof; and c) isolating the protein.

Combining the sequence of step a) with a heavy chain variable region of an antibody or fragment thereof can be carried out in different aspects. Examples are two polypeptide chains which are linked to each other covalently or non-covalently, one polypeptide chain such as a fusion protein of heavy and light chain domains directly connected with or without a peptide linker, and two polypeptide chains which are subsequently cross-linked by UV light and/or chemical linkers.

The amino acid sequence motif DDD within CDR1 of the light chain variable region is crucial for the effect of binding a calcium ion as shown in examples 4 and 5. The sequence is derived from the murine germ line gene IGKV17-121*01. The sequence IGKV17-121*01 (SEQ ID NO:1) itself can be used as fixed VL gene.

The sequence motif DDD within CDR1 of the light chain variable region (CDR-L1) does not automatically result in metal ion dependent binding. A sequence search in a public databases reveals that some antibodies and antibody fragments contain this sequence motif, but obviously do not own the capability of metal ion binding at the antigen binding interface. For example, for a Vk17-light chain based Fv fragment which binds epidermal growth factor peptide, the crystal structure does not contain a metal ion, although the DDD sequence motif and even a potential metal ion coordination site similar to Q425 is present (Zhou et al. 2005). Therefore, besides the sequence motif DDD within CDR-L1, a screening method is required to isolate those proteins from a library or pool of proteins having the sequence motif DDD which bind to a given antigen in a metal ion dependent manner.

In the case of LT1009, the aspartate residue within CDR3 of the light chain is also involved in Ca2+ dependent antigen binding. Therefore the method of the present invention may also include a light chain variable region which has at least one aspartate residue in CDR3.

In one aspect of the present invention the light chain variable region of an antibody for the generation of metal ion binding proteins as disclosed herein has the amino acid sequence motif DDD within CDR1. Preferentially, the light chain variable region has the amino acid sequence motif DDD at position 36-38 in CDR1 (IMGT nomenclature). More preferentially, the light chain variable region has the amino acid sequence motif DDD at position 36-38 in CDR1 (IMGT nomenclature) and an additional D in CDR3. Most preferentially, the light chain variable region has the amino acid sequence motif DDD at position 36-38 in CDR1 (IMGT nomenclature) and an additional D at position 108 in CDR3 (IMGT nomenclature).

In another aspect of the present invention the light chain variable region of an antibody for the generation of metal ion binding proteins has the amino acid sequence motif DxDDD within CDR1, wherein x represents every possible amino acid residue. Preferentially, the light chain variable region has the amino acid sequence motif DxDDD in CDR1, wherein the first D is at position 28 and the DDD motif is at position 36-38 (IMGT nomenclature) and x represents every possible amino acid residue. More preferentially, the light chain variable region has the amino acid sequence motif DxDDD in CDR1 and an additional D in CDR3, wherein in CDR1 the first D is at position 28 and the DDD motif is at position 36-38 (IMGT nomenclature) and x represents every possible amino acid residue. Most preferentially, the light chain variable region has the amino acid sequence motif DxDDD in CDR1 and an additional D in CDR3, wherein in CDR1 the first D is at position 28 and the DDD motif is at position 36-38 (IMGT nomenclature) and x represents every possible amino acid residue, and wherein in CDR3 the D is at position 108 (IMGT nomenclature).

In another aspect of the present invention the light chain variable region of an antibody for the generation of metal ion binding proteins has at least 50% identity to a sequence selected from the group consisting of SEQ ID NO:1, SEQ ID NO:2 and SEQ ID NO:3. Preferentially, the light chain variable region has at least 70% identity to a sequence selected from the group consisting of SEQ ID NO:1, SEQ ID NO:2 and SEQ ID NO:3. More preferentially, the light chain variable region has at least 90% identity to a sequence selected from the group consisting of SEQ ID NO:1, SEQ ID NO:2 and SEQ ID NO:3. In addition more preferentially, the light chain variable region is SEQ ID NO:1 or SEQ ID NO:2 or SEQ ID NO:3. Most preferentially, the light chain variable region is SEQ ID NO:1.

Besides $Ca^{2+}$, also other metal ions can be bound by a metal ion binding protein. In the case of Q425, $Sr^{2+}$ and $Cd^{2+}$ ions are also able to bind to a certain degree. In the case of LT1002, it was found that the antibody binds also $Mg^{2+}$ and $Ba^{2+}$ ions to a certain degree. Therefore, the method of the present invention is not limited to $Ca^{2+}$ ions, but may also include other metal ions. Examples are, but not limited to, $Ca^{2+}$, $Mg^{2+}$, $Zn^{2+}$, $Mn^{2+}$, $Sr^{2+}$, $Ba^{2+}$, $K^+$, $Cu^{2+}$, $Co^{2+}$, $Cd^{2+}$. Preferentially, the ion is selected from the group consisting of $Ca^{2+}$, $Mg^{2+}$, $Zn^{2+}$, $Mn^{2+}$, $Sr^{2+}$, $Ba^{2+}$, $K^+$. More preferentially, the ion is a divalent cation selected from the group consisting of $Ca^{2+}$, $Mg^{2+}$, $Zn^{2+}$, $Mn^{2+}$, $Sr^{2+}$, $Ba^{2+}$. In addition preferentially, the ion is a divalent cation selected from the group consisting of $Ca^{2+}$ and $Mg^{2+}$. Most preferentially, the ion is $Ca^{2+}$.

An essential feature of this invention is the synergistic effect of the combination of an amino acid sequence motif within the light chain of the protein and a method to isolate the metal ion binding protein. For the isolation of metal ion binding proteins, methods are used that allow the identification and subsequent isolation of the specific proteins within a pool of proteins comprising metal ion binding and metal ion independent proteins. Examples for such methods are high-throughput ELISA screening, high-throughput cell-based screening, phage display selection, and yeast display selection.

The method of the present invention may be used with any technology known in the art to generate the recombinant protein such as antibodies or fragments thereof. Such technologies are in vitro display technologies such as phage display, ribosome display, mRNA display, yeast display, bacterial display, *E. coli* display, C is display, DNA display, covalent display, B-cell display.

If a method such as a display technology is used to generate the proteins of the present invention, a multiple depletion step, at least one-fold, more preferred two- or more-fold, may be performed to select and isolate metal ion binding proteins.

The metal ion binding protein may be an antibody or fragment thereof.

The proteins generated by the method of the present invention may be used in subsequent applications which may take benefit of the property of metal ion dependency of the proteins. These metal ion binding proteins are preferentially compatible with the strict requirements of cell culture conditions where cells are usually kept within a narrow pH range at nearly neutral pH.

Such an application may be for example the enrichment, purification and isolation of recombinant proteins. Another example is the magnetic cell sorting technology such as MACS® (U.S. Pat. No. 5,411,863, U.S. Pat. No. 5,543,289, U.S. Pat. No. 6,020,210, U.S. Pat. No. 6,417,011). The proteins of the present invention may be coupled to a solid support such as magnetic beads, the cells which present the antigen on their surface are bound by the magnetic beads and are retained in the magnetic field. The cells may then be eluted in the presence of substances which binds to and/or complex the metal ions, thereby removing them from the protein. These substances include, but are not limited to, the class of chelating agents such as EDTA or EGTA and the class of metal ion precipitating agents such as oxalate or molybdate.

Another subsequent application is the reversible staining or labeling of cells with antibodies generated with the method of the present invention and coupled to a fluorescent dye. The labeling may be dissolved in the presence of an chelating agent such as EDTA or EGTA or of an precipitating agent such as oxalate or molybdate.

Therefore, it is an object of the present invention to provide the use of metal ion binding proteins for enrichment and isolation of recombinant proteins or reversible labeling of cells.

In the state of the art there is no disclosure of recombinantly expressed antibodies or antibody fragments such as Fab or scFv molecules which were intentionally generated to bind an antigen in a $Ca^{2+}$ dependent manner. The only disclosure is a $Ca^{2+}$ dependent hCD4 reactive monoclonal antibody clone Q425 and a $Ca^{2+}$ dependent-sphingosine-1-phosphate (S1P) Fab fragment LT1009, derived by enzymatic proteolysis of a monoclonal antibody, having a specificity for the lipid.

Contrary to the method of the present invention, the property of $Ca^{2+}$ dependency of antigen binding of both proteins was generated accidentally using methods for generating antibodies or antibody fragments without the intention to generate calcium ion binding antibodies or antibody fragments. Therefore, the present invention provides metal ion binding proteins such as antibodies and antibody fragments, wherein the interaction with their bindings partners such as antigens can be controlled by the addition and removal or complexation of the metal ion.

The coding sequences of the metal ion binding proteins generated by the method of the present invention may be further used for the expression of the metal ion binding proteins in a cellular system or a cell-free expression system. In one application, recombinant antibodies and fragments thereof which have metal ion binding properties are produced.

Anti-CD8 proteins were generated with the method of the present invention. Therefore, it is an object of the present invention to provide a metal ion binding anti-CD8 protein. In one aspect of the present invention the anti-CD8 protein binds an ion selected from the group consisting of $Ca^{2+}$, $Mg^{2+}$, $Zn^{2+}$, $Mn^{2+}$, $Sr^{2+}$, $Ba^{2+}$, $K^+$, $Cu^{2+}$, $Co^{2+}$, $Cd^{2+}$. Preferentially, the anti-CD8 protein binds an ion selected from the group consisting of $Ca^{2+}$, $Mg^{2+}$, $Zn^{2+}$, $Mn^{2+}$, $Sr^{2+}$, $Ba^{2+}$, $K^+$. More preferentially, the anti-CD8 protein binds a divalent cation selected from the group consisting of $Ca^{2+}$, $Mg^{2+}$, $Zn^{2+}$, $Mn^{2+}$, $Sr^{2+}$, $Ba^{2+}$. In addition preferentially, the anti-CD8 protein binds a divalent cation selected from the group consisting of $Ca^{2+}$ and $Mg^{2+}$. Most preferentially, the anti-CD8 protein binds $Ca^{2+}$.

In another aspect of the present invention the anti-CD8 protein is an antibody or fragment thereof. Preferentially, the anti-CD8 protein comprises the CDR regions of SEQ ID NO:1 combined with either SEQ ID NO:4 or SEQ ID NO:5. Most preferentially, the anti-CD8 protein comprises SEQ ID NO:1 combined with either SEQ ID NO:4 or SEQ ID NO:5.

DEFINITIONS

Unless defined otherwise, technical and scientific terms used herein have the same meaning as commonly understood by one of ordinary skill in the art to which this invention belongs.

As used herein, the term "antibody or fragment thereof" is intended to include polyclonal and monoclonal antibodies, chimeric and humanized antibodies, natural and recombinant antibodies, antibody fragments, and molecules which are antibody equivalents in that they specifically bind to an epitope on the product antigen. The term "antibody" includes polyclonal and monoclonal antibodies of any isotype (IgA, IgG, IgE, IgD, IgM) and mutants thereof, or an antigen-binding portion thereof, including, but not limited to, Fab and Fv fragments such as Fab, Fab', F(ab')2, scFv, Fv, Bis-scFv, diabody, triabody, tetrabody, minibody, and single chain antibodies. It also comprises libraries of antibodies and antibody fragments.

As used herein, the term "antigen" is intended to include substances that evoke the production of one or more antibodies. Each antibody binds to a specific antigen by way of an interaction similar to the fit between a lock and a key. The substance may be from the external environment or formed within the body. The term "antigen" comprises, but is not limited to, proteins, peptides, polypeptides, oligopeptides, lipids, carbohydrates, and combinations thereof, for example a glycosylated protein.

As used herein, the term "display technology" comprises methods and technologies that are able to link genotype and phenotype in one particle. The term "display technology" includes, but is not limited to, phage display, ribosome display, mRNA display, DNA display, CIS display, covalent display, yeast display, bacterial display, and B-cell display.

As used herein, the term "library" is intended to include collections of nucleic acids fragments such as DNA and RNA, wherein this collection is stored and propagated in a population of micro-organisms and/or particles. Such particles can be, for example, phages. In another embodiment, the term "library" is also used for to the collection of all of the cloned vector molecules, wherein these vector molecules comprise the collection of nucleic acids fragments.

As used herein, the terms "panning" and "biopanning" comprise affinity selection methods and techniques which selects for molecules such as peptides and proteins that bind to a given target.

As used herein, the terms "DNA shuffling" and "chain shuffling" comprise methods and techniques for the in vitro recombination of different antibody genes. For example a VH gene repertoire is combined directed or undirected with a given VL gene repertoire or vice versa.

As used herein, the term "CDR" or "complementarity determining region" is intended to define regions within antibodies or T cell receptors where these proteins complement an antigen's shape. Thus, CDRs determine the protein's affinity and specificity for specific antigens. The CDRs are the most variable part of the molecule, and contribute to the diversity of these molecules, allowing the antibody and the T cell receptor to recognize a vast repertoire of antigens. According to the IMGT nomenclature (ImMunoGeneTics Information System®, http://www.imgt.org), the CDRs of antibodies comprise the following amino acid positions: CDR1: 27-38; CDR2: 56-65; CDR3: 105-116 (germline)/ 105-117 (rearranged).

As used herein, the term "IMGT nomenclature" describes the numbering scheme of antibody sequences according to IMGT (ImMunoGeneTics Information System®), see FIG. 1A.

As used herein, the term "IGKV" is used as abbreviation for immunoglobulin kappa variable region gene.

As used herein, the terms "VH", "VL" and "VHH" are used as abbreviations for the variable region of the antibody heavy chain ("VH"), the variable region of the antibody light chain ("VL"), and the variable region of a single domain antibody found in camelids ("VHH").

As used herein, the term "metal ions" is intended to comprise, but not limited to, $Ca^{2+}$, $Mg^{2+}$, $Zn^{2+}$, $Mn^{2+}$, $Sr^{2+}$, $Ba^{2+}$, $K^+$, $Cu^{2+}$, $Co^{2+}$, $Cd^{2+}$.

As used herein, the term "PBMC" is used as abbreviation for a peripheral blood mononuclear cell, which is any blood cell having a round nucleus. Examples are lymphocytes, monocytes and macrophages.

As used herein, the term "target molecule" is intended to include the binding partner of interest as well as substances, molecules, complexes or entities that contain the binding partner of interest. The term "target molecule" comprises, but is not limited to, a eukaryotic cell, a prokaryotic cell, fragments of cells, an artificial cell, or a complex of an antigen immobilized to a matrix.

As used herein, the term "binding partner" is intended to include molecules that are bound by proteins such as antibodies, especially by metal ion dependent proteins. These binding partners include, but are not limited to, antigens, natural proteins, recombinant proteins, polypeptides, peptides, lipids, glycoproteins, and lipoproteins.

As used herein, the term "metal ion binding protein" comprises proteins which bind simultaneously a binding partner and a metal ion, wherein the metal ion is required for the binding of the protein to the binding partner. As a result, the binding reaction is depending on the metal ion. Preferentially, the metal ion is located in the interface between the metal ion binding protein and its binding partner. In the absence of the metal ion binding protein, the binding partner may not have to bind to the metal ion per se.

As used herein, the term "screening method" is intended to include methods to identify individuals that show previously defined properties. It comprises the characterization of single individuals such as single clones or products derived from single clones for example in a suitable assay. As an example for such an assay, supernatants of *E. coli* single clones (derived from phage display selection) may be screened for binding of secreted antibody fragments against a given antigen. Binding could be detected by methods known in the art such as, for example, ELISA or flow cytometry.

As used herein, the term "chelating agent" comprises substances, chemicals and molecules that form soluble, complex molecules with certain metal ions, inactivating the ions so that they cannot normally react with other elements or ions to produce precipitates or scale. They include, but are not limited to, EDTA (ethylenediaminetetraacetic acid), EGTA (ethylene glycol tetraacetic acid), DOTA (1,4,7,10-tetraazacyclododecane-1,4,7,10-tetraacetic acid), DTPA (diethylenetriaminepentaacetic acid), and phosphonates.

As used herein, the term "precipitating agent" is intended to include substances and molecules that have the ability to form salts or complexes with metal ions, wherein the formed salt or complex has a low solubility in aqueous solution. The term "precipitating agent" includes, but is not limited to, phosphate, pyrophosphate, fluoride, molybdate, carbonate, ferrocyanide, hydroxide, selenite, citrate, and oxalate.

As used herein, the term "identity" (of proteins) is used for a comparison of proteins chains: two proteins are identical if they contain the same amino acid residues in the same order. The degree of identity is defined by the difference in amino acid residues. For example, for two proteins which are 90% identical, 90% of the amino acid residues are identical. The degree of identity is usually determined by alignment of sequences and calculation of % identity using standard molecular biology software tools.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that aspects and variations of the invention described herein include "consisting" and/or "consisting essentially of" aspects and variations.

The method of the present invention may also be used to generate metal ion binding proteins other than Ca2+ binding proteins. The selection method described here to isolate Ca2+ binding proteins is not limited to Ca2+ ions, but can also be used with other metal cations simply by exchanging Ca2+ with another cation. Examples are, but not limited to, Ca2+, Mg2+, Zn2+, Mn2+, Sr2+, Ba2+, K+, Cu2+, Co2+, Cd2+. The CD4 Q425 antibody is also able to bind Sr2+ and Cd2+, and the antibody LT1002, is also able to bind Mg2+ and Ba2+ ions, indicating that the cation is not limited to Ca2+.

The method of the present invention is not limited to the usage of a murine light chain sequence. Similar sequences from other organisms having the relevant sequence elements for binding metal ions can also be used. Examples are, but not limited to, sequences from human, rat, hamster, chicken, horse, cattle, pig and llama. Compared to SEQ ID NO:1, SEQ ID NO:2 is the nearest light chain homologue sequence from human, containing the DDD motif in CDR-L1 and the aspartate residue in CDR-L3, having a sequence identity of 65%. SEQ ID NO:3 is the nearest light chain homologue sequence from rat, containing the DDD motif in CDR-L1 and the aspartate residue in CDR-L3, having a sequence identity of 86%. Similar sequences contain the DDD motif in CDR-L1 and an aspartate residue in CDR-L3 and are at least 50% identical to SEQ ID NO:1, more preferred at least 70% identical, and most preferred at least 90% identical.

The method of the present invention is also not limited to the usage of a light chain sequence. Sequences similar to light chain sequences having the relevant sequence elements for binding metal ions can also be used. For example, llama antibodies contain only two heavy chains which are capable of binding antigens. SEQ ID NO:5 describes the sequence of a llama immunoglobulin heavy chain variable region which contains the DDD motif within CDR1 and an aspartate residue within CDR3.

EMBODIMENTS

In a preferred embodiment of the present invention antibody phage display is used to generate Ca2+ binding proteins. First a laboratory animal (e.g. BALB/c mouse) is immunized with the antigen of choice. The antigen is, for example, a protein or cells bearing the antigen on the surface. Afterwards, B-cells of the animal are isolated and B-cell cDNA is generated. Then antibody genes are amplified by PCR using proper primer sets. The amplified antibody VH genes are combined with the VL gene of IGKV17-121 resulting in an antibody gene library. This library is used in phage display selection using immobilized antigen of choice and proper panning conditions (e.g. Ca2+ containing buffers) to enrich specific binders. Using chelating or metal ion precipitating agents, Ca2+ binding proteins which were bound to the antigen can be dissociated and eluted. To enhance the efficiency of selecting a Ca2+ dependent binder, depletion steps can be performed towards the final selection step.

In one embodiment of the present invention, the animal is not only immunized with the antigen of choice, but metal ions may are also be administered to the animal. This may result in a higher frequency of metal ion binding antibodies produced in the animal.

The animal may be for example an avian species such as chicken or a mammalian species such as mouse, rat, rabbit, or human.

In another embodiment of the present invention, non-immunized donors are used to generate VH diversity. To ensure diversity IgG VH genes are not amplified but the IgM repertoire of B-cells is utilized to gain diversity. Since in this naïve approach no "priming" against the antigen occurs the selection system has to be very efficient to enrich binders against the antigen of choice.

In another embodiment of the present invention, alternative display technologies such as ribosome or yeast display are used to enrich metal ion binding proteins.

In another embodiment of the present invention, high-throughput screening such as automated multi-well single clone screening is used to identify and isolate metal ion binding proteins from a library or pool of proteins.

In another embodiment of the present invention, metal cations other than Ca2+ are used to generate metal ion binding proteins. Examples are, but not limited to, Ca2+, Mg2+, Zn2+, Mn2+, Sr2+, Ba2+, K+, Cu2+, Co2+, Cd2+.

In another embodiment of the present invention, metal ion binding proteins are generated which are useful for the reversible labeling of a target molecule. Binding of the protein occurs in the presence of the metal ion, while absence or removal of the metal ion results in dissociation of the protein from its target. Target molecules can be, for example, cells in solution or cells in tissues which may be reversibly labeled by the protein. This is useful for reversible fluorescent and/or magnetic labeling of cells which can be achieved by coupling the metal binding protein to a fluorescent or and/magnetic label. In one example, a fluorochrome conjugate of a metal ion binding antibody is incubated with cells of which at least some carry the antigen which can be specifically bound by the metal binding antibody. In the absence of the metal ion, no binding of the antibody fluorochrome conjugate to its antigen and therefore no labeling of the target cells occurs. Addition of metal ions results in binding of the antibody fluorochrome conjugate to its antigen and specific cell labeling. Further addition of a chelating agent such as EDTA or a precipitating agent leads to dissociation of the antibody fluorochrome and its antigen and hence target cells are not labeled any more. In a further step, metal ions can be added to specifically label the target cells again, and EDTA or a precipitating agent can be added once more to remove the label again. This procedure can be repeated until a concentration of one of the added reagents is reached which is toxic for cells.

In another embodiment of the present invention, metal ion binding proteins are used for the specific purification and isolation of binding partners, for example purification of proteins by affinity chromatography and isolation of cells by magnetic cell sorting such as MACS® technology with subsequent removal of the magnetic label. In both embodiments, the metal ion binding protein is usually immobilized, for example conjugated to a matrix such as sepharose or a magnetic bead. A solution containing the binding partner is incubated with the metal ion binding protein in the presence of the metal ion.

In the case of protein purification by affinity chromatography, the sepharose with immobilized metal ion binding protein, for example a Ca2+ binding anti-polyhistidine antibody, is washed to remove unbound material. The binding partner, for example a recombinant protein containing a polyhistidine tag, is eluted by adding a solution comprising a metal chelating agent such as EDTA. As a result, a purified protein free of the Ca2+ binding anti-polyhistidine antibody is obtained. In contrast to conventional elution of polyhistidine tagged proteins which are eluted from a polyhistidine tag binding material such as Ni2+ chelate complexes with an access of imidazole, the present invention allows an elution of the polyhistidine tagged protein free of imidazole.

In the case of magnetic cell sorting with MACS®, magnetic beads are coupled with the protein of the present invention, for example a Ca2+ binding anti-CD8 antibody. A solution containing CD8+ cells such as PBMC is incubated with these beads and applied to a column placed within a magnetic field. The cells unbound to the magnetic beads flow through the column, while the cells expressing CD8 on their surface are retained on the column by the beads via the anti-CD8 antibody. After a washing step, CD8+ cells are eluted giving a solution containing a chelating agent such as EDTA or a precipitating agent. As a result a CD8+ cell population substantially free of the Ca2+ binding anti-CD8 antibody and substantially free of magnetic beads is obtained. The procedure is exemplified by the MACS® technology but no limitation to this specific technology is intended.

In another embodiment of the invention an isolated nucleic acid coding for metal ion binding protein is provided.

In another embodiment a host cell such as a prokaryotic, eukaryotic or yeast cell harboring an isolated nucleic acid coding for metal ion binding protein is provided.

In another embodiment of the invention a recombinantly produced metal ion binding antibody or antibody fragment such as Fab or scFv is provided that is capable to bind its antigen in a metal ion dependent manner. Preferably this antibody or antibody fragment comprises an amino acid sequence based on an allele that contains aspartate residues capable of binding metal cations.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Example 1

Immunization of Mice with CD8 Protein

For intraperitoneal immunization recombinant extracellular domain of human CD8a protein (Ser 22-Asp 182), fused with a C-terminal polyhistidine tag and expressed in human cells, was used. Prior to immunization hCD8a was alum precipitated. With aluminum precipitation the soluble antigen is converted into a precipitate with aluminum hydroxide, which acts as adjuvant to boost immune reaction. Therefore, 200 μg lyophilized hCD8a was reconstituted first in 0.5 mL dH20 and mixed with 0.5 mL 10% $KAl(SO_4)_2$. pH was adjusted to pH 8-9, which led to protein precipitation. After an incubation time of 1 h at 4° C., the sample was centrifuged for 10 min at 4° C. and 16,000×g. Afterwards, the supernatant was collected and the pellet was washed two times with 1.5 mL PBS (phosphate buffered saline) and centrifuged for 10 min at 4° C. and 16,000×g. Finally, the protein was resuspended in 0.63 mL PBS and stored at 4° C. until immunization. The efficiency of alum precipitation was controlled by measuring the protein concentration of the supernatant using Bradford assay. Two seven weeks old female BALB/c mice were intraperitoneally (IP) immunized with 29 microgram alum precipitated hCD8a at three time points, on day 0, day 14 and day 21. Spleens were dissected on day 24.

Example 2

Amplification of Variable Antibody Genes

Figure 2:
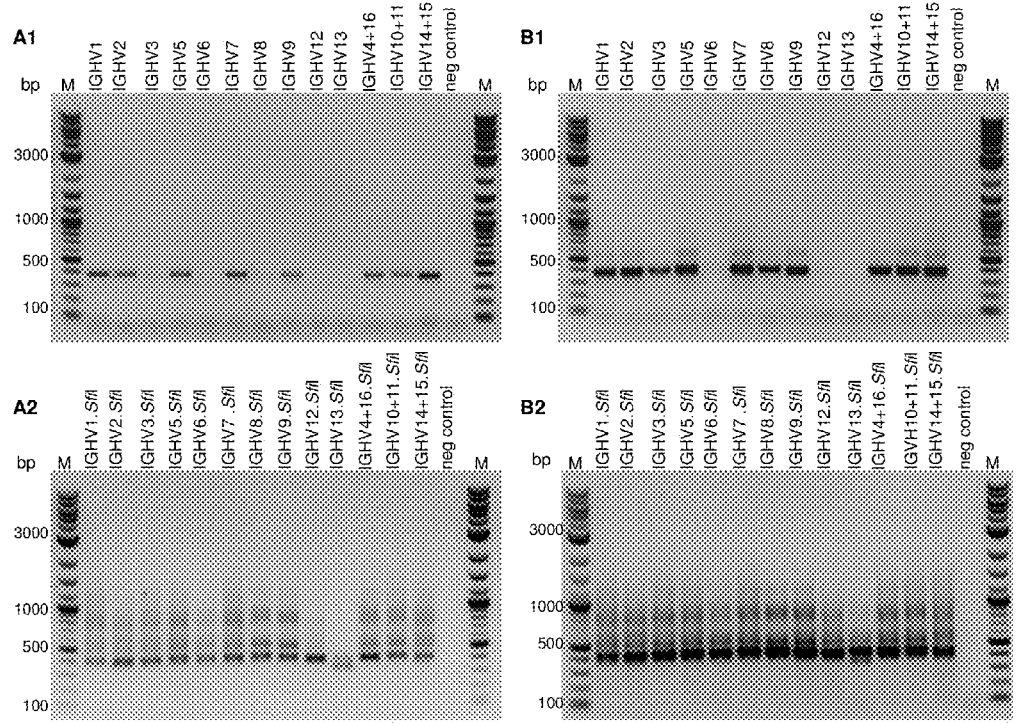
FIG. 2 shows amplification of variable heavy chain antibody genes. VH PCR products were analyzed by agarose gel electrophoresis. The amplification was carried out using partial degenerate oligonucleotides sets in a two-step PCR. PCR was performed using Taq DNA polymerase and an annealing temperature of 55° C. (first PCR) and 60° C. (second PCR). Every primer combination was applied in a separate reaction, purified by gel extraction and applied as template in a second PCR. The expected sizes of PCR products are approx. 360 bp after first PCR and approx. 390 bp after second PCR. As negative control nuclease-free water was used in a reaction with IGHV1 forward primer.
Figure 9:
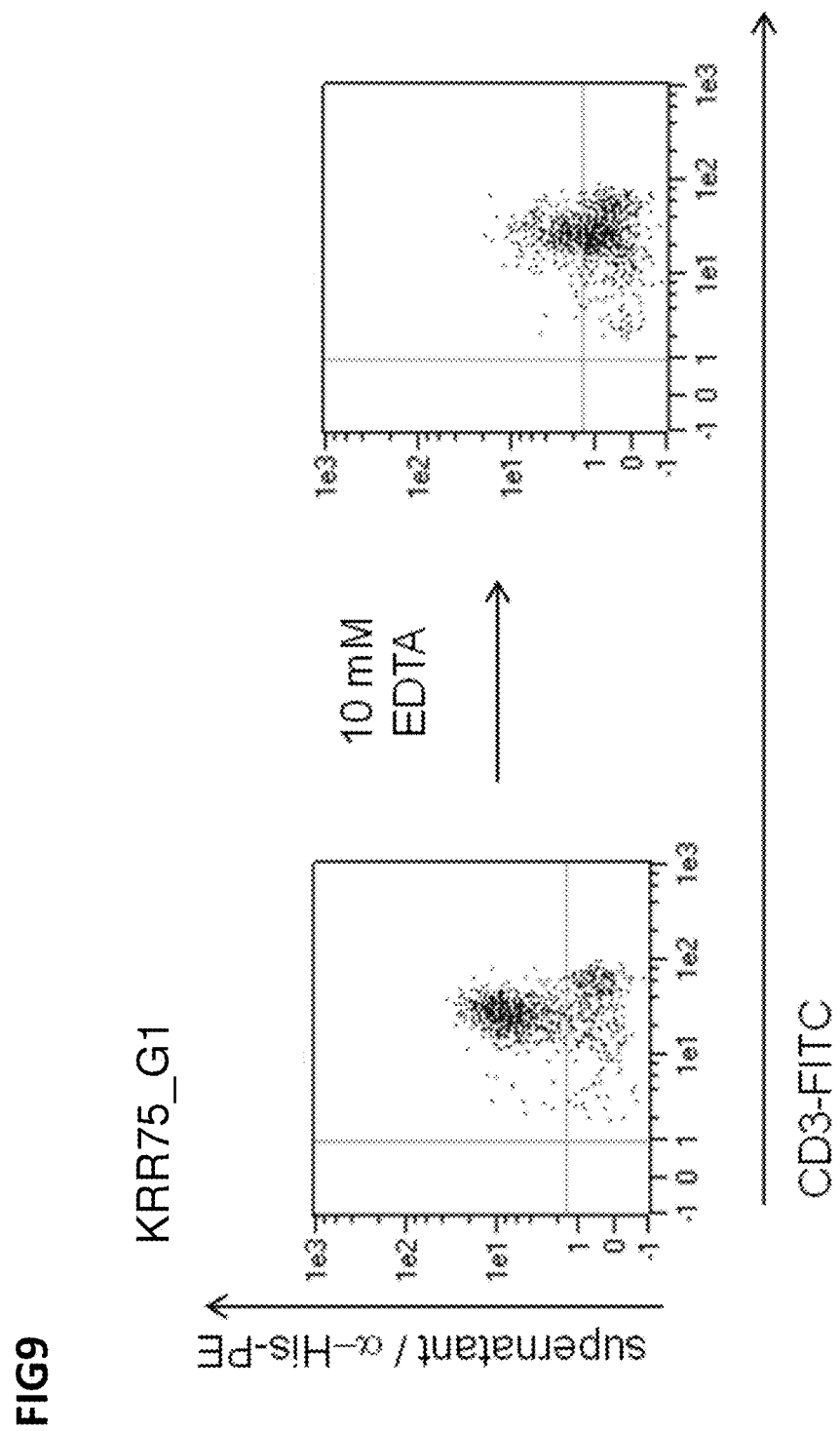
Figure 10:
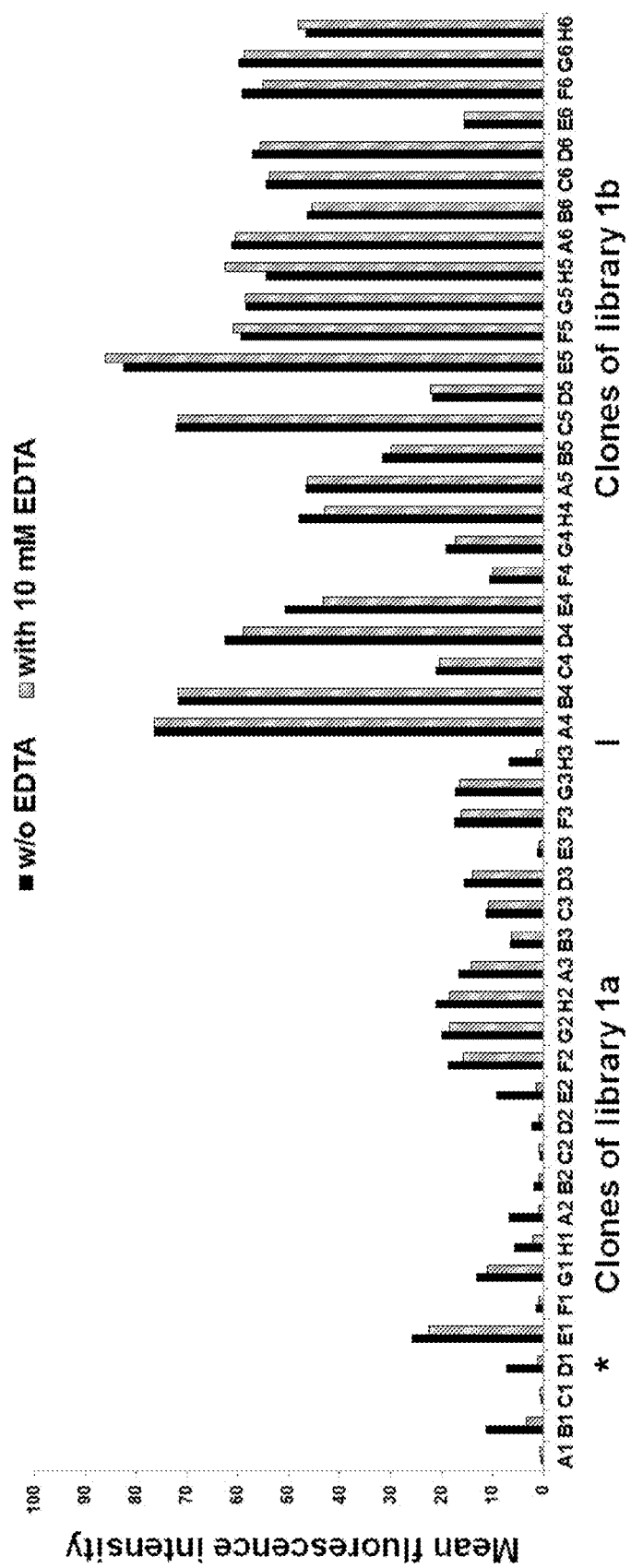
FIGS. 10, 11, and 12 show flow cytometry results of screened clones after panning cycle IIIb. Flow cytometry results of screened clones (see 4.4.2.2) of library 1a and 2a from EDTA eluates after panning cycle IIIb. After exclusion of dead cells and cell debris CD8+ cells were identified as a CD3+/CD4– cell population. hCD8 specific Fabs were detected by anti-His-PE. Mean fluorescence intensities (MFI) of anti-His-PE staining were plotted to evaluate the influence of 10 mM EDTA on staining with certain Fab clones. 77_A1 (uninoculated medium) and 77_C1 (anti-MUC1 scFv expressing clone) were negative controls, while 77_B1 (CD8 BW135/80) served as positive control for hCD8 staining.
Figure 11:
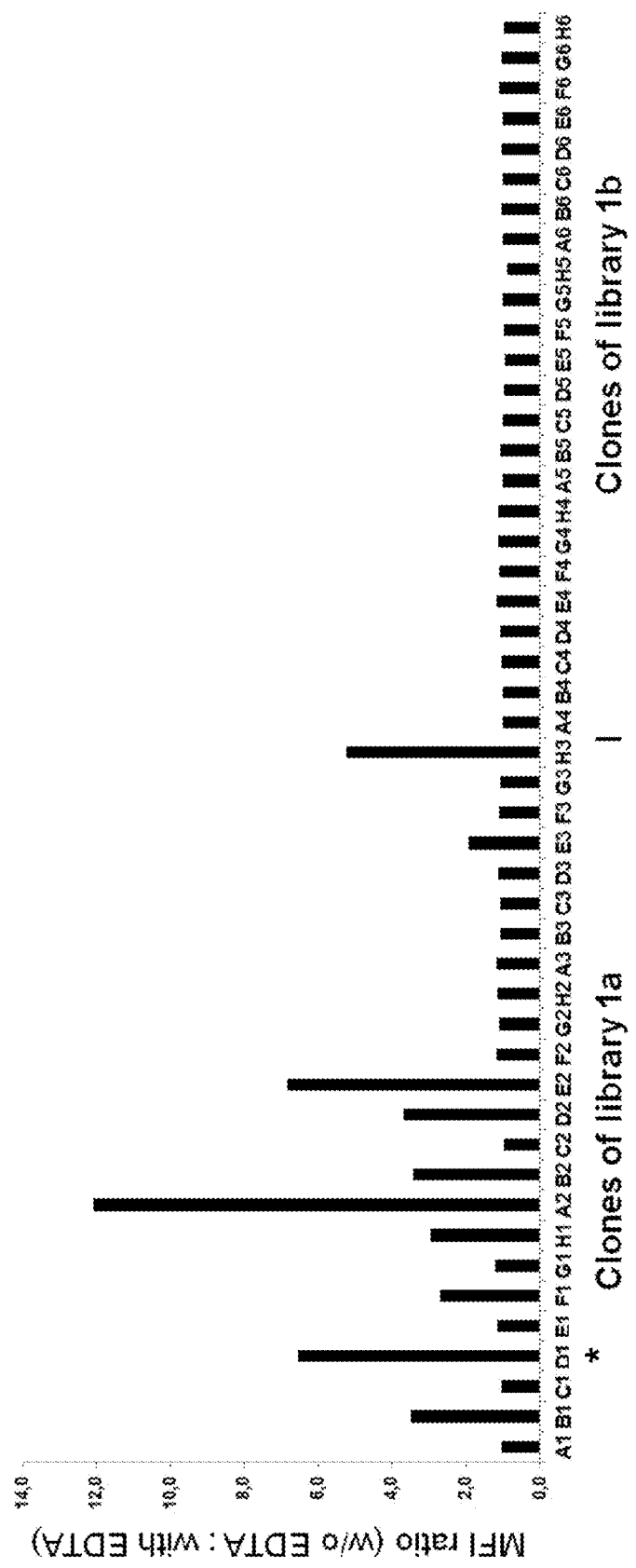
Figure 12:
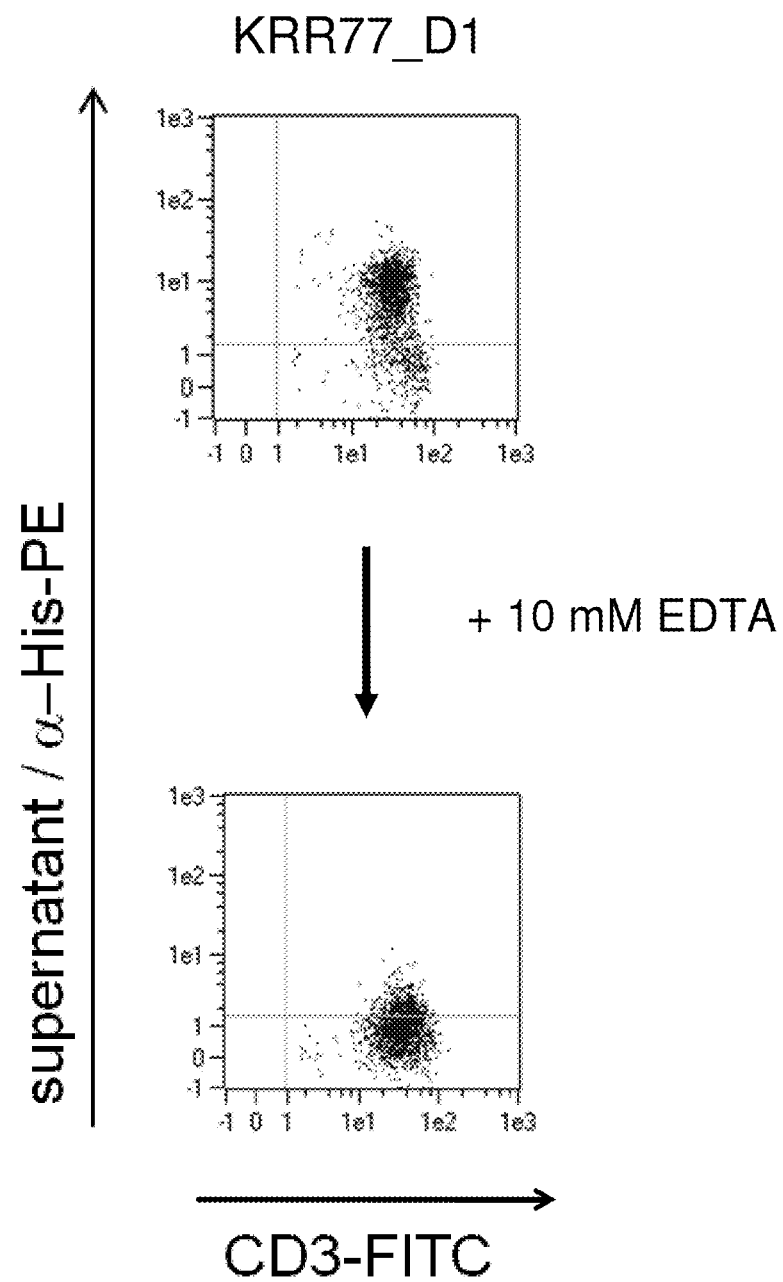

Amplifications of heavy (IgG1, IgG2a, IgG2b) and light chain (kappa) variable antibody genes were performed in a two-step PCR using degenerate primer sets. These primer sets consist of 13 (VH) or 14 (VL) different forward primer hybridizing with antibody variable regions and one reverse primer binding at the beginning of constant region. Every primer combination was applied in a separate reaction. After first PCR round DNA separated on a 1% agarose gel was separately purified via gel extraction and applied as template in a second PCR reaction. The second PCR step is necessary for the addition of parts of leader sequences (PelB or PhoA) and restriction sites at 5' end for following cloning steps. PCR products (FIG. 2) were finally purified using a gel extraction kit and pooled.

Example 3

Phage Display Selection

Clones from immune libraries were selected for hCD8a binding activity using phage display. In this attempt antibody phage repertoires were first incubated with the appropriate antigen. This step was performed as solid phase approach with hCD8a immobilized on plastic surface or in solution with biotinylated hCD8a followed by streptavidin-bead incubation. After removal of unspecific binders, hCD8a specific antibody phages were eluted with trypsin or alternatively with 10 mM EDTA to obtain clones with Ca2+ dependent binding activity.

According to standard panning protocol two or three panning cycles with decreasing antigen concentrations and increasing number of washing steps were performed to investigate, whether an isolation of hCD8a specific phages is possible. After every panning cycle numbers of eluted antibody phages (cfu) were determined (FIG. 3 and FIG. 4). In the first panning cycle phages presenting Fab fragments in an oligovalent manner were used (assembly with Hyperphage).

Variations in panning process were tested to direct the selection towards Ca2+ dependent binding. Therefore, Ca2+ independent hCD8a specific phages were depleted by incubation with hCD8a in presence of 10 mM EDTA. Unbound phages were subsequently precipitated to remove EDTA and were used in a further panning cycle in presence of Ca2+ followed by EDTA elution. Besides one-step depletion, three-step depletions with higher antigen concentrations each were performed to enhance depletion efficiency. The phage titer of EDTA elutions ($2.8 \times 10^4$–$1 \times 10^7$) tended to be lower than in the standard panning procedure; this was expected because of previous depletion step(s). However, phage titer of experiments with single or triple depletion(s) did not differ at all (FIG. 5 and FIG. 6).

Example 4

Single Clone Characterization

Clones generated by different selection procedures and stages were characterized upon hCD8 specificity and potential Ca2+ dependent binding. Therefore, Fab expressions of single clones were performed in a microtiter plate format (150 µL). Supernatants of these cultures were analyzed for the presence hCD8 specific Fabs using a flow cytometric staining assay in the Ca2+ containing buffer HBSS (Hank's balanced salt solution)+0.5% BSA. As target cells human PBMCs were used, while CD8+ cells were identified as a CD3+ and CD4– cell population. Bound Fabs were detected via the polyhistidine tag of the Fab and an anti-polyhistidine tag-fluorochrome conjugate. Clones showing a Ca2+ dependent binding were identified by flow cytometry before and after addition of EDTA to a final concentration of 10 mM (FIG. 7-FIG. 12).

Example 5

Characterization of Purified Chimeric Recombinant Fabs

Figure 13:
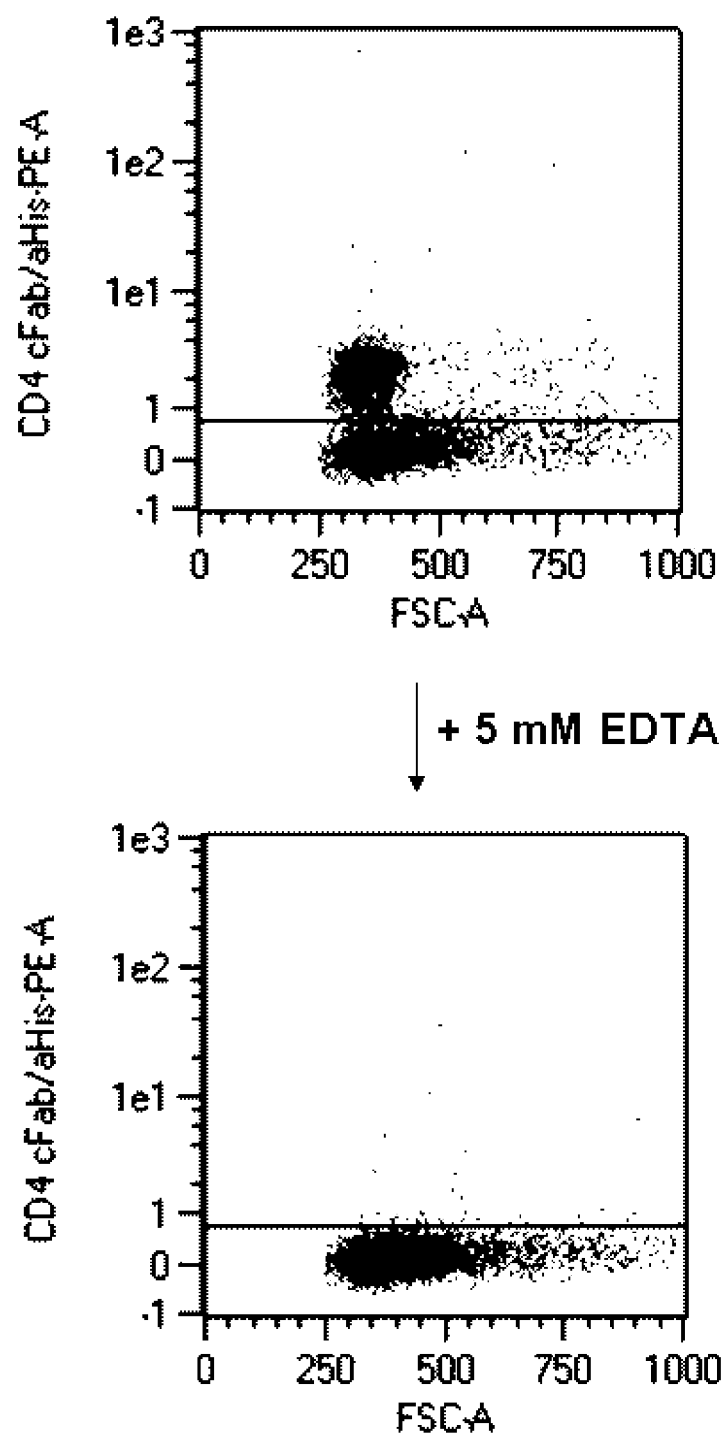
FIG. 13 shows flow cytometry results of PMBC staining with purified chimeric recombinant Fab CD4 Q425. Fab was detected by anti-His-PE. Mean fluorescence intensities (MFI) of anti-His-PE staining were plotted to evaluate the influence of 5 mM EDTA on staining with certain chimeric Fab CD4 Q425.
Figure 15:
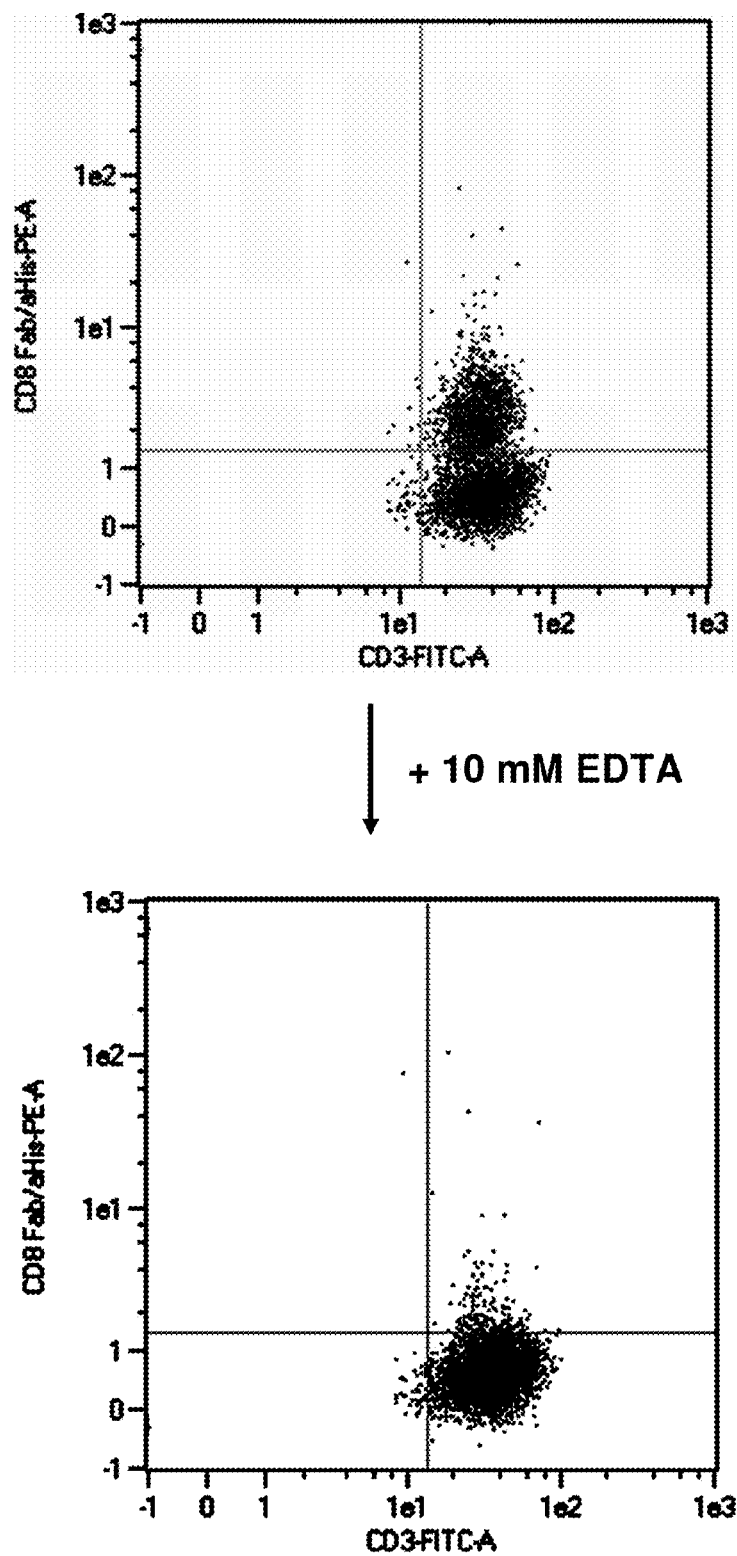
FIG. 15 shows flow cytometry results of PMBC staining with purified chimeric recombinant CD8 KRR77_D1. Fab was detected by anti-His-PE. Mean fluorescence intensities (MFI) of anti-His-PE staining were plotted to evaluate the influence of 10 mM EDTA on staining with certain chimeric Fab CD8 KRR77_D1.

Genes encoding for Fab sequences of CD4 Q425, CD8 KRR75_G1 and CD8 KRR77_D1 were cloned in a suitable *E. coli* expression vector by standard molecular biology techniques. Afterwards chimeric Fabs comprising constant domains of human origin were produced in *E. coli* using standard techniques. Fabs were purified using affinity chromatographic techniques. Purified recombinant Fabs were used at a defined concentration (10 µg/mL) for flow cytometry experiments using the Ca2+ containing buffer HBSS+ 0.5% BSA. Human PBMCs were used as target cells, while CD8+ cells were identified as a CD3+ CD4– cell population. Bound Fabs were detected via the polyhistidine tag of the Fab and an anti-polyhistidine tag-fluorochrome conjugate. Ca2+ dependency of binding was shown by the addition of EDTA to a final concentration of 5-10 mM (FIG. 13-FIG. 15)

The invention claimed is:

1. A method for the targeted generation of antibodies or fragments thereof that bind antigen in a Ca2+ or Mg2+ dependent manner, the method comprising: a) combining SEQ ID No: 1 or a fragment comprising the CDRs of SEQ ID NO: 1 with antibody heavy chain variable regions; b) screening for antibodies that bind antigen in a Ca2+ or Mg2+ dependent manner; and c) identifying individual antibodies or antigen binding fragments thereof that bind antigen in a Ca2+ or Mg2+ dependent manner.

2. The method of claim 1, wherein said step b) is performed by a method selected from the group consisting of high-throughput ELISA screening, high-throughput cell-based screening, phage display selection, and yeast display selection.

3. The method of claim 1, wherein said step c) is performed by ELISA or flow cytometry.

* * * * *

```
SEQUENCE LISTING

<160> NUMBER OF SEQ ID NOS: 10

<210> SEQ ID NO 1
<211> LENGTH: 107
<212> TYPE: PRT
<213> ORGANISM: Mus musculus
<220> FEATURE:
<223> OTHER INFORMATION: IGKV17-121*01 with IGKJ4*01

<400> SEQUENCE: 1

Glu Thr Thr Val Thr Gln Ser Pro Ala Ser Leu Ser Met Ala Ile Gly
1               5                   10                  15

Glu Lys Val Thr Ile Arg Cys Ile Thr Ser Thr Asp Ile Asp Asp Asp
                20                  25                  30

Met Asn Trp Tyr Gln Gln Lys Pro Gly Glu Pro Pro Lys Leu Leu Ile
            35                  40                  45

Ser Glu Gly Asn Thr Leu Arg Pro Gly Val Pro Ser Arg Phe Ser Ser
        50                  55                  60

Ser Gly Tyr Gly Thr Asp Phe Val Phe Thr Ile Glu Asn Met Leu Ser
65                  70                  75                  80

Glu Asp Val Ala Asp Tyr Tyr Cys Leu Gln Ser Asp Asn Leu Pro Phe
                85                  90                  95

Thr Phe Gly Ser Gly Thr Lys Leu Glu Ile Lys
            100                 105

<210> SEQ ID NO 2
<211> LENGTH: 107
<212> TYPE: PRT
<213> ORGANISM: Homo sapiens
<220> FEATURE:
<223> OTHER INFORMATION: IGKV5-2 (IGKV5-2*01) with IGKJ2*01 65 %
      (70/107) identity to SEQ ID NO:1 (ClustalW2)

<400> SEQUENCE: 2

Glu Thr Thr Leu Thr Gln Ser Pro Ala Phe Met Ser Ala Thr Pro Gly
```

```
              1               5                  10                 15
            Asp Lys Val Asn Ile Ser Cys Lys Ala Ser Gln Asp Ile Asp Asp
                            20                  25                 30

Met Asn Trp Tyr Gln Gln Lys Pro Gly Glu Ala Ala Ile Phe Ile Ile
                            35                  40                 45

Gln Glu Ala Thr Thr Leu Val Pro Gly Ile Pro Pro Arg Phe Ser Gly
                        50                  55                 60

Ser Gly Tyr Gly Thr Asp Phe Thr Leu Thr Ile Asn Asn Ile Glu Ser
            65                  70                  75                 80

Glu Asp Ala Ala Tyr Tyr Phe Cys Leu Gln His Asp Asn Phe Pro Leu
                                85                  90                 95

Thr Phe Gly Gly Gly Thr Lys Val Glu Ile Lys
                            100                 105

<210> SEQ ID NO 3
<211> LENGTH: 107
<212> TYPE: PRT
<213> ORGANISM: Rattus norvegicus
<220> FEATURE:
<223> OTHER INFORMATION: IGKV17S1*01 with IGKJ4*01 86 % (92/107)
      identity to SEQ ID NO:1 (ClustalW2)

<400> SEQUENCE: 3

Glu Thr Thr Val Thr Gln Ser Pro Ala Ser Leu Ser Met Ala Val Gly
            1               5                  10                 15

Glu Lys Val Ser Ile Ser Cys Lys Thr Ser Thr Asp Ile Asp Asp Asp
                            20                  25                 30

Met Asn Trp Tyr Gln Gln Lys Ser Gly Glu Ala Pro Lys Leu Leu Ile
                            35                  40                 45

Ser Glu Gly Asn Thr Leu Arg Pro Gly Val Pro Ser Arg Phe Ser Ser
                        50                  55                 60

Ser Gly Tyr Gly Thr Asp Phe Val Phe Thr Ile Asn Asn Val Leu Leu
            65                  70                  75                 80

Gly Asp Glu Gly Ile Tyr Tyr Cys Gln Gln Ser Asp Asn Val Pro Phe
                                85                  90                 95

Thr Phe Gly Ser Gly Thr Lys Leu Glu Ile Lys
                            100                 105

<210> SEQ ID NO 4
<211> LENGTH: 118
<212> TYPE: PRT
<213> ORGANISM: Mus musculus
<220> FEATURE:
<223> OTHER INFORMATION: Amino acid sequence of VH derived from clone
      KRR75_G1

<400> SEQUENCE: 4

Glu Val Gln Leu Gln Gln Ser Gly Pro Glu Leu Val Lys Pro Gly Ala
            1               5                  10                 15

Ser Val Lys Met Ser Cys Lys Ala Ser Gly Tyr Thr Phe Thr Asp Tyr
                            20                  25                 30

Val Ile Ser Trp Met Lys Gln Arg Thr Gly Gln Gly Leu Glu Trp Ile
                            35                  40                 45

Gly Glu Ile Tyr Pro Gly Ser Gly Ser Asp Tyr Tyr Asn Glu Lys Phe
                        50                  55                 60

Lys Gly Lys Ala Thr Leu Thr Ala Asp Lys Ser Ser Asn Thr Ala Tyr
            65                  70                  75                 80

Met Gln Leu Ser Ser Leu Thr Ser Glu Asp Ser Ala Val Tyr Phe Cys
```

```
                        85                  90                  95

Ala Arg Trp Gly Ile Thr Asp Tyr Phe Asp Val Trp Gly Ala Gly Thr
            100                 105                 110

Thr Val Thr Val Ser Ser
        115

<210> SEQ ID NO 5
<211> LENGTH: 116
<212> TYPE: PRT
<213> ORGANISM: Mus musculus
<220> FEATURE:
<223> OTHER INFORMATION: Amino acid sequence of VH derived from clone
      KRR77_D1

<400> SEQUENCE: 5

Gln Val Gln Leu Lys Glu Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Ser Pro Gly Lys Gly Leu Glu Trp Leu
        35                  40                  45

Gly Val Ile Trp Arg Gly Gly Ser Thr Asp Tyr Asn Ala Ala Phe Met
    50                  55                  60

Ser Arg Leu Ser Ile Thr Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Lys Asn Ser Ile Thr Pro Phe Ala Tyr Trp Gly Gln Gly Thr Leu Val
            100                 105                 110

Thr Val Ser Ala
        115

<210> SEQ ID NO 6
<211> LENGTH: 115
<212> TYPE: PRT
<213> ORGANISM: Lama glama
<220> FEATURE:
<223> OTHER INFORMATION: Amino acid sequence of immunoglobulin heavy
      chain variable region, (IGHV gene), clone W342, from Lama glama
      (llama). GenBank entry AJ237377.1.

<400> SEQUENCE: 6

Leu Gln Ala Ser Gly Gly Gly Leu Val Gln Ala Gly Gly Ser Leu Arg
1               5                   10                  15

Leu Ser Cys Ala Ala Ser Gly Phe Ser Phe Asp Asp Tyr Val Ile
            20                  25                  30

Gly Trp Phe Arg Gln Ala Pro Gly Lys Gly Arg Glu Gly Ile Ala Cys
        35                  40                  45

Ile Arg Trp His Asp Ser His Ile Asn Thr Glu Asp Ser Val Lys Gly
    50                  55                  60

Arg Phe Thr Ile Ser Gly Asp Asn Ala Lys Asn Ala Val Tyr Leu Gln
65                  70                  75                  80

Met Asn Ser Leu Asn Pro Glu Asp Thr Ala Val Tyr Phe Cys Ala Ala
                85                  90                  95

Gly Ser Ser Gly Leu Lys Gly Pro Tyr Asp Tyr Trp Gly Gln Gly Thr
            100                 105                 110

Gln Val Thr
        115
```

<210> SEQ ID NO 7
<211> LENGTH: 107
<212> TYPE: PRT
<213> ORGANISM: Homo sapiens
<220> FEATURE:
<223> OTHER INFORMATION: Q425 VL

<400> SEQUENCE: 7

```
Glu Thr Thr Val Thr Gln Ser Pro Ala Ser Leu Ser Val Ala Ile Gly
1               5                  10                  15

Glu Lys Val Thr Ile Arg Cys Ile Thr Ser Thr Asp Ile Asp Asp Asp
            20                  25                  30

Met Asn Trp Tyr Gln Gln Lys Pro Gly Glu Pro Pro Lys Phe Phe Ile
        35                  40                  45

Ser Glu Gly Asn Thr Leu Arg Pro Gly Val Pro Ser Arg Phe Ser Ser
    50                  55                  60

Ser Gly Tyr Gly Thr Asp Phe Val Phe Thr Ile Glu Asn Met Leu Ser
65                  70                  75                  80

Glu Asp Val Ala Asp Tyr Tyr Cys Leu Gln Ser Asp Thr Leu Pro Leu
                85                  90                  95

Thr Phe Gly Ser Gly Thr Lys Leu Glu Ile Lys
            100                 105
```

<210> SEQ ID NO 8
<211> LENGTH: 107
<212> TYPE: PRT
<213> ORGANISM: Mus musculus
<220> FEATURE:
<223> OTHER INFORMATION: LT1002 (= LT1002 VL)

<400> SEQUENCE: 8

```
Glu Thr Thr Val Thr Gln Ser Pro Ala Ser Leu Ser Met Ala Ile Gly
1               5                  10                  15

Glu Lys Val Thr Ile Arg Cys Ile Thr Thr Thr Asp Ile Asp Asp Asp
            20                  25                  30

Met Asn Trp Phe Gln Gln Lys Pro Gly Glu Pro Pro Asn Leu Leu Ile
        35                  40                  45

Ser Glu Gly Asn Ile Leu Arg Pro Gly Val Pro Ser Arg Phe Ser Ser
    50                  55                  60

Ser Gly Tyr Gly Thr Asp Phe Leu Phe Thr Ile Glu Asn Met Leu Ser
65                  70                  75                  80

Glu Asp Val Ala Asp Tyr Tyr Cys Leu Gln Ser Asp Asn Leu Pro Phe
                85                  90                  95

Thr Phe Gly Ser Gly Thr Lys Leu Glu Ile Lys
            100                 105
```

<210> SEQ ID NO 9
<211> LENGTH: 107
<212> TYPE: PRT
<213> ORGANISM: Rattus norvegicus
<220> FEATURE:
<223> OTHER INFORMATION: IGKV17S1*01

<400> SEQUENCE: 9

```
Glu Thr Thr Val Thr Gln Ser Pro Ala Ser Leu Ser Met Ala Val Gly
1               5                  10                  15

Glu Lys Val Ser Ile Ser Cys Lys Thr Ser Thr Asp Ile Asp Asp Asp
            20                  25                  30

Met Asn Trp Tyr Gln Gln Lys Ser Gly Glu Ala Pro Lys Leu Leu Ile
```

```
                   35                  40                  45
Ser Glu Gly Asn Thr Leu Arg Pro Gly Val Pro Ser Arg Phe Ser Ser
            50                  55                  60

Ser Gly Tyr Gly Thr Asp Phe Val Phe Thr Ile Asn Asn Val Leu Leu
65                  70                  75                  80

Gly Asp Glu Gly Ile Tyr Tyr Cys Gln Gln Ser Asp Asn Val Pro Leu
                85                  90                  95

Thr Phe Gly Ser Gly Thr Lys Leu Glu Ile Lys
            100                 105

<210> SEQ ID NO 10
<211> LENGTH: 107
<212> TYPE: PRT
<213> ORGANISM: Homo sapiens
<220> FEATURE:
<223> OTHER INFORMATION: IGKV5-2*01

<400> SEQUENCE: 10

Glu Thr Thr Leu Thr Gln Ser Pro Ala Phe Met Ser Ala Thr Pro Gly
1               5                   10                  15

Asp Lys Val Asn Ile Ser Cys Lys Ala Ser Gln Asp Ile Asp Asp Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys
            100                 105
```